(12) United States Patent
Davies et al.

(10) Patent No.: US 6,962,891 B2
(45) Date of Patent: Nov. 8, 2005

(54) SOLID SUPPORT DIRHODIUM CATALYST COMPOSITIONS AND METHODS FOR MAKING AND USING SAME

(75) Inventors: Huw M. L. Davies, Clarence Center, NY (US); Tadamichi Nagashima, Allison Park, PA (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 10/229,392

(22) Filed: Aug. 27, 2002

(65) Prior Publication Data

US 2003/0130112 A1 Jul. 10, 2003

Related U.S. Application Data

(60) Provisional application No. 60/315,147, filed on Aug. 27, 2001.

(51) Int. Cl.[7] .................................................. B01J 31/00
(52) U.S. Cl. ........................ 502/159; 502/167; 502/104; 502/166; 502/171; 548/403; 546/2
(58) Field of Search ................................. 502/159, 166, 502/171, 104, 150, 127; 548/403; 546/2; 518/701; 423/22; 252/182.33

(56) References Cited

U.S. PATENT DOCUMENTS

| | | | |
|---|---|---|---|
| 2,507,631 A | | 5/1950 | Hartmann et al. |
| 2,957,880 A | | 10/1960 | Rometsch et al. |
| 4,133,881 A | | 1/1979 | Cale, Jr. et al. |
| 4,238,488 A | | 12/1980 | Howe et al. |
| 4,866,048 A | | 9/1989 | Calverley et al. |
| 5,036,053 A | | 7/1991 | Himmelsbach et al. |
| 5,175,311 A | | 12/1992 | Doyle |
| 5,296,595 A | | 3/1994 | Doyle |
| 5,302,737 A | * | 4/1994 | Doyle et al. ................. 556/436 |
| 5,401,732 A | | 3/1995 | Calverley et al. |
| 5,591,854 A | * | 1/1997 | Davies ......................... 546/14 |
| 5,665,890 A | | 9/1997 | Jacobsen et al. |
| 5,760,055 A | | 6/1998 | Davies |
| 5,789,333 A | | 8/1998 | Angelici et al. |
| 6,025,502 A | | 2/2000 | Winklter et al. |
| 6,410,746 B1 | * | 6/2002 | Davies ......................... 548/403 |
| 6,420,304 B1 | * | 7/2002 | Tsai et al. .................... 502/207 |

FOREIGN PATENT DOCUMENTS

| | | |
|---|---|---|
| GB | 2 260 903 A | 5/1993 |
| WO | WO 00/64583 | 11/2000 |

OTHER PUBLICATIONS

Doyle, et al. "Dirhodium (II) Tetrakis'methyl 2–oxaazetidine–4–carboxylate': A Chiral Dirhodium (II) Carboxamidate of Exception Reactivity and Selectivity", Organic Letters 2(8), 1145–1147.*

Bertilsson et al. "A Rigid Dirhodium (II) Carboxylate as an Efficient Catalyst for the Asymmetric Cyclopropanation of Olefins", J. Organometallic Chemistry 603 (2000), 13–17.*

Davies et al. "Kinetic Resolution and Double Stereodifferentiation in Catalytic Asymmetric C–H Activation of 2–Substituted Pyrrolidines", Organic Letters 3(1), 1773–1775.*

Doyle et al. "Cyclopropanation versus carbon–hydrogen insertion. The influences of substrate and catalyst on selectivity", Tetrahedron Letters 42 (2001), 3155–3158.*

Davies, et al. "Conformational analysis and stereochemical assignments of products from C–H activation at secondary sites", Tetrahedron Letters 42 (2001), 3149–3151.*

Bulugahapitiya, et al. "A Stereospecific Access to Alylic Systems Using Rhodium (II)–Vinyl Carbenoid Insertion into Si–H, O–H, and N–H Bonds", J. Org. Chem. 62 (1997), 1630–1641.*

Aggarwal, et al. "Catalytic Cyclopropanation of Alkenes Using Diazo Compounds Generated in Situ. A Novel Route to 2–Acrylcyclopropylamines", Organic Letters 3(17) 2785–2788.*

Claimes 1–104 of copending US 2003/0130536.*

Davies, et al. "Rhodium (II) (S)–N–(arylsufonyl)prolinate catalyzed asymmetric insertions of vinyl– and phenylcarbenoids into the Si–H bond", Tetrahedron Letters, 38 (10), 1741–1744.*

Davies, et al. "Asymmetric synthesis of the tremulane skeleton by a tandem cyclopropanation/cope rearrangement", Tetrahedron Letters, 37 (23), 3967–3970.*

Davies, et al. "Effect of diazoalkane structure on the stereoselectivity of Rhodium (II) (S)–N–(arylsulfonyl)prolinate catalyzed cyclopropanations", Tetrahedron Letters, 37 (24), 4133–4136.*

(Continued)

Primary Examiner—J. A. Lorengo
Assistant Examiner—Jennine Brown
(74) Attorney, Agent, or Firm—Rogalskyj & Weyand, LLP

(57) ABSTRACT

Disclosed are dirhodium catalyst compositions. One such dirhodium catalyst composition includes a dirhodium catalyst and a solid support. The dirhodium catalyst includes a Rh—Rh moiety and four bridging ligand moieties. The dirhodium catalyst and the solid support are bound together, but they are not covalently bound together via one or more of the bridging ligand moieties. Another such dirhodium catalyst composition includes a dirhodium tetracarboxylate catalyst and a solid support, and the dirhodium tetracarboxylate catalyst and the solid support are bound together. Yet another such dirhodium catalyst composition includes a dirhodium catalyst and a solid support, where the dirhodium catalyst includes a Rh—Rh moiety and where the dirhodium catalyst and the solid support are bound together via at least one of the rhodiums' axial positions. The compositions can be used in a number of reactions, including insertion reactions (e.g., C—H insertions, Si—H insertions, O—H insertions, and N—H insertions), cyclopropanation reactions, annulations (e.g., [3+2] annulations and [3+4] annulations), and ω,ω-diarylalkanoate synthesis. Methods for making the dirhodium catalyst compositions are also disclosed.

54 Claims, No Drawings-

OTHER PUBLICATIONS

Doyle, et al. "Chiral catalysts for enantioselective intermolecular cyclopropanation reactions with methyl phenyldiazoacetate. Origin of the solvent effect in reactions catalyzed by homochiral Dirhodium (II) Prolinates", Tetrahedron Letters, 37 (24), 4129.*

Davies, et al. "Asymmetric Cyclopropanations by Rhodium (II) N–(Arylsulfonyl)prolinate Catalyzed Decomposition of Vinyldiazomethanes in the Presence of Alkenes . . ." JACS (1996), 118, 6897–6907.*

Colacot, Thomas. "An overview on the applications of 'Doyle catalysts' in asymmetric cyclopropanation, cyclopropenation and C H insertion reactions", Proc. Indian Acad. Sci. (Chem. Sci.), 112 (3), 197–207.*

Colacot, "An Overview on the Applications of 'Doyle Catalysts' in Asymmetric Cyclopropanation, Cyclopropenation and C–H Insertion Reactions," Proc. Indian Acad. Sci. (Chem. Sci. ), 112(3):197–207 (2000).

Doyle et al., "A New Class of Chiral Lewis Acid Catalysts for Highly Enantioselective Hetero–Diels–Alder Reactions: Exceptionally High Turnover Numbers from Dirhodium(II) Carboxamidates," J. Am. Chem. Soc., 123:5366–5367 (2001).

Doyle et al., "Enantioselective Metal Carbene Transformations with Polyethylene–Bound Soluble Recoverable Dirhodium(II) 2–Pyrrolidone–5(S)–carboxylates," J. Org. Chem., 57:6103–6105 (1992).

Andersen et al., "Preparation and Catalytic Properties of Resin Bound Binuclear Rhodium Tetracarboxylate Complexes," Tetrahedron Letters, 39:7815–7818 (1998).

Burguete et al., "Polymer–supported Bis(oxazoline)–copper Complexes as Catalysts in Cyclopropanation Reactions," Org. Lett., 2(24):3905–3908 (2000).

Glos et al., "Aza–bis(oxazolines): New Chiral Ligands for Asymmetric Catalysis," Org. Lett., 2(14):2045–2048 (2000).

Annuziata et al., "Poly(ethylene glycol)–Supported Bisoxazolines as Ligands for Catalytic Enantioselective Synthesis," J. Org. Chem., 66(9):3160–3666 (2001).

Burguete et al., "Bis(oxazoline)copper Complexes Covalently Bonded to Insoluble Support as Catalysts in Cyclopropanation Reactions," J. Org. Chem., 66(26):8893–8901 (2001).

Nagashima et al., "Catalytic Asymmetric Solid–phase Cyclopropanation," J. Am. Chem. Soc., 123: 2695–2696 (2001).

Nowotny et al., "Heterogeneous Dinuclear Rhodium(II) Hydroformylation Catalysts—Performance Evaluation and Silsesquioxane–Based Chemical Modeling," Angew. Chem. Int. Ed., 40(5):955–958 (2001).

Orlandi et al., "An Insoluble Polymer–Bound Bis–Oxazoline Copper(II) Complex: A Highly Efficient Heterogeneous Catalyst for the Enantioselective Mukaiyama Aldol Reaction," Angew. Chem. Int. Ed. Engl., 40(13):2519–2521 (2001).

Rechavi et al., "Heterogenization of a Chiral Bis(oxazoline) Catalyst by Grafting onto Silica," Org. Lett., 3(16):2493–2496 (2001).

Davies et al., "Recent Progress in Asymmetric Intermolecular C–H Activation by Rhodium Carbenoid Intermediates," J. Organometallic Chem., 617–618:47–55 (2001).

Davies, et al., "Catalytic Asymmetric C–H Activation of Alkanes and Tetrahydrofuran," J. Am. Chem. Soc., 122(13):3063–3070 (2000).

Davies et al., "Catalytic Asymmetric Synthesis of Diarylacetates and 4,4–Diarybutanoates. A Formal Asymmetric Synthesis of (+)–Sertraline," Organic Letters, 2(3):417–417 (2000).

Davies et al., "Effect of Rhodium Carbenoid Structure on Cyclopropanation Chemoselectivity," Tetrahedron, 56:4871–4880 (2000).

Davies, et al., "Effect of Carbenoid Structure on the Reactions of Rhodium–Stabilized Carbenoids with Cycloheptatriene," Tetrahedron Letters, 41:2035–2038 (2000).

Davies et al., "Stereoselectivity of Methyl Aryldiazoacetate Cyclopropanations of 1,1–Diarylethylene. Asymmetric Synthesis of a Cyclopropyl Analogue of Tamoxifen," Organic Letters, 2(6):823–826 (2000).

Dias et al., "Short Synthesis of Methylphenidate and Its p–Methoxy Derivative," Synthetic Communications, 30(7):1311–1318 (2000).

Müller et al., "Intermolecular Cyclopropanation Versus CH Insertion in RhII–Catalyzed Carbenoid Reactions," Tetrahedron, 56:1725–1731 (2000).

Davies et al., "Asymmetric Intramolecular C–H Insertions of Aryidiazoacetates," Organic Letters, 3(10):1475–1477 (2001).

Davies et al., "Catalytic Asymmetric C–H Activation of Silyl Enol Ethers as an Equivalent of an Asymmetric Michael Reaction," J. Am. Chem. Soc., 123(9):2070–2071 (2001).

Davies et al., "Catalytic Asymmetric Synthesis of Highly Functionalized Cyclopentenes by a [3+2] Cycloaddition," J. Am. Chem. Soc., 123(30):7461–7462 (2001).

Davies et al., "Improved Dirhodium Tetraprolinate Catalysts for Asymmetric Reactions of Diazocarbonyl Compounds," abstract No. 249 in Abstracts of the 222nd ACS National Meeting, Chicago, Illinois, Aug. 26–30, 2001, American Chemical Society, Division of Organic Chemistry (2001).

Davies et al., "Kinetic Resolution and Double Stereodifferentiation in Catalytic Asymmetric C–H Activation of 2–Substituted Pyrrolidines," Organic Letters, 3(11):1773–1775 (2001).

Davies, "'3+4' Annulations Between Rhodium–stabilized Vinylcarbenoids and Dienes," Advances in Cycloaddition, 5:119–164 (1999).

Davies, et al. "Catalytic Asymmetric Synthesis of Diarylacetates and 4,4–Diarylbutanoates. A Formal Asymmetric Synthesis of (+)– Sertraline," Organic Letters, 1(2):233–236 (1999).

Davies, et al., "Catalytic Asymmetric Synthesis of Syn–Aldol Products from Intermolecular C–H Insertions Between Allyl Silyl Ethers and Methyl Aryldiazoacetates," Organic Letters, 1(3):383–385 (1999).

Davies, "Dirhodium Tetra(N–arylsulfonylprolinates) as Chiral Catalysts For Asymmetric Transformations of Vinyl– and Aryldiazoacetates," Eur. J. Org. Chem., 2459–2469 (1999).

Davies et al., "Enantioselective Synthesis of Fused Cycloheptadienes by a Tandem Intramolecular Cyclopropanation/Cope Rearrangement Sequence," J. Org. Chem., 64(23):8501–8508 (1999).

Davies et al., "Highly Regio–, Diastereo–, and Enantioselective C–H Insertions of Methyl Aryldiazoacetates into Cyclic N–Boc–Protected Amines. Asymmetric Synthesis of Novel C2–Symmetric Amines and threo–Methylphenidate," J. Am. Chem Soc., 121(27):6509–6510 (1999).

Davies, et al., "Novel Dirhodium Tetraprolinate Catalysts Containning Bridging Prolinate Ligands for Asymmetric Carbenoid Reactions," *Tetrahedron Letters*, 40:5287–5290 (1999).

Deutsch, et al., "Synthesis and Pharmacology of Site–Specific Cocaine Abuse Treatment Agents: 2–(Aminomethyl)–3–phenylbicyclo'2.2.2'– and –'2.2.1'alkane Dopamine Uptake Inhibitors," *J. Med. Chem.*, 42:882–895 (1999).

Deutsch et al., "Synthesis and Pharmacology of Site–Specific Cocaine Abuse Treatment Agents: The Role of the Phenyl Group in Highly Modified Methylphenidate Analogs As Dopamine Uptake Inhibitors," *Medicinal Chemistry Research*, 9(4):213–222 (1999).

Matsumura, et al., "A Convenient Method for Synthesis of Enantiomerically Enriched Methylphenidate from N–Methoxycarbonylpiperidine," *Organic Letters*, 1(2):175–178 (1999).

Prashad, et al., "Enantioselective Synthesis of (2s, 2'R)–erythro–methylphenidate," *Tetrahedron: Asymmetry*, 10:3479–3482 (1999).

Prashad, et al., "The First Enantioselective Synthesis of (2R,2'R)–threo–(+)–Methylphenidate Hydrochloride," *J. Org. Chem.*, 64:1750–1753 (1999).

Davies et al., "Asymmetric Intermolecular Carbenoid C–H Insertions Catalyzed by Rhodium(II) (S)–N–(p–Dodecylphenyl)sulfonylprolinate," *J. Am. Chem. Soc.*, 119:9075–9076 (1997).

Davies, "Asymmetric Synthesis Using Rhodium–Stabilized Vinylcarbenoid Intermediates," *Aldrichimica Acta*, 30(4):107–114 (1997).

Davies et al., "Enantioselective Synthesis of Functionalized Tropanes by Rhodium(II) Carboxylate–Catalyzed Decomposition of Vinyldiazomethanes in the Presence of Pyrroles," *Journal of Organic Chemistry*, 62(4):1095–1105 (1997).

Davies et al., "Synthesis and Evaluation of a Novel Dirhodium Tetraprolinate Catalyst Containing Bridging Prolinate," *Tetrahedron Letters*, 38(24):4203–4206 (1997).

Axten, et al., "A Stereoselective Synthesis of di–threo–Methylphenidate: Preparation and Biological Evaluation of Novel Analogues," *J. Org. Chem.*, 63:9628–9629 (1998).

Davies et al., "Effect of Carbenoid Structure on the Reactivity of Rhodium Stabilized Carbenoids," *Tetrahedron Letters*, 39:4417–4420 (1998).

Davies et al., "Effect of Catalyst on the Diastereoselectivity of Metal Phenyldiazoacetate Cyclopropanations," *Tetrahedron Letters*, 39:8811–8812 (1998).

Davies, "Rhodium–Stabilized Vinylcarbenoid Intermediates in Organic Synthesis," *Current Organic Chemistry*, 2:463–488 (1998).

Davies et al., "Tandem Asymemtric Cyclopropanation/Cope Rearrangement. A Highly Diastereoselective and Enantioselective Method for the Construction of 1,4–Cycloheptadienes," *J. Am. Chem. Soc.*, 120(14):3326–3331 (1998).

Stinson, "Counting on Chiral Durgs," *Chemical & Engineering News*, pp. 83ff (Sep. 21, 1998).

Thai et al., "Asymmetric Synthesis and Pharmacology of Methylphenidate and Its Para–Substituted Derivatives," *J. Med. Chem.*, 41:591–601 (1998).

Axten, et al., "Enantioselective Synthesis of D–threo–Methylphenidate," *J. Am. Chem Soc.*, 121(27):6511–6512 (1999).

Deutsch, et al., "Synthesis and Pharmacology of Potential Cocaine Antagonists. 2. Structure—Activity Relationship Studies of Aromatic Ring–Sustituted Methylphenidate Analogs," *J. Med. Chem.*, 39:1201–1209 (1996).

Doyle et al., "Chiral Catalysts for Enantioselective Intermolecular Cyclopropanation Reactions With Methyl Phenyldiazoacetate. Origin of the Solvent Effect in Reactions Catalyzed by Homochiral Dirhodium(II) Prolinates," *Tetrahedron Letters*, 37(24):4129–4132 (1996).

Davies et al., "Asymmetric Cyclopropanations by Rhodium(II) N–(Arylsulfonyl)prolinate Catalyzed Decomposition of Vinyldiazomethanes in the Presence of Alkenes. Practical Enantioselective Synthesis of the Four Isomers of 2–Phenylcyclopropan–1–amimo Acid," *J. Am. Chem. Soc.*, 118(29):6897–6907 (1996).

Davies et al., "Effect of Diazoalkane Structure on the Stereoselectivity of Rhodium (II) (S)–N–(Arylsulfonyl)prolinate Catalyzed Cyclopropanations," *Tetrahedron Letters*, 37(24):4133–4136 (1996).

* cited by examiner

US 6,962,891 B2

SOLID SUPPORT DIRHODIUM CATALYST COMPOSITIONS AND METHODS FOR MAKING AND USING SAME

This application claims the benefit of U.S. Provisional Patent Application Ser. No. 60/315,147, filed Aug. 27, 2001, which is hereby incorporated by reference.

The present invention was made with the support of the National Science Foundation, Contract No. CHE 0092490, and the National Institutes of Health, Contract No. CA85641 and Contract No. GM57425. The Federal Government may have certain rights in this invention.

FIELD OF THE INVENTION

The present invention relates, generally, to metal catalyst compositions and to methods for using such compositions and, more particularly, to compositions containing dirhodium catalyst on a solid support and to methods for using such compositions.

BACKGROUND OF THE INVENTION

Dirhodium catalysts have been employed as catalysts in a variety of chemical reactions. One of the major drawbacks of using dirhodium catalysts is the expense of rhodium metal. Typically, to overcome the costs associated with catalysts containing expensive metals, two approaches can be used: (i) increasing the efficiency (e.g., turnover number and/or turnover rate) of the catalyst and/or (ii) recovering the spent catalyst from the reaction mixture so that the expensive metal can be separated and recycled. Neither approach has had much success with chiral dirhodium catalysts.

The present invention is directed to dirhodium catalyst compositions in which a dirhodium catalyst is attached to a solid support, for example, to facilitate recovery of spent catalyst from a reaction mixture.

SUMMARY OF THE INVENTION

The present invention relates to a dirhodium catalyst composition which includes a dirhodium catalyst and a solid support. The dirhodium catalyst includes a Rh—Rh moiety and four bridging ligand moieties. The dirhodium catalyst and the solid support are bound together, but they are not covalently bound together via one or more of the bridging ligand moieties.

The present invention also relates to a dirhodium catalyst composition which includes a dirhodium tetracarboxylate catalyst and a solid support, and the dirhodium tetracarboxylate catalyst and the solid support are bound together.

The present invention also relates to a dirhodium catalyst composition which includes a dirhodium catalyst and a solid support. The dirhodium catalyst includes a Rh—Rh moiety, and the dirhodium catalyst and the solid support are bound together via at least one of the rhodiums' axial positions.

DETAILED DESCRIPTION OF THE INVENTION

The present invention, in one aspect thereof, relates to a dirhodium catalyst composition which includes a dirhodium catalyst and a solid support. The dirhodium catalyst includes a Rh—Rh moiety and four bridging ligand moieties. The dirhodium catalyst and the solid support are bound together, but they are not covalently bound together via one or more of the bridging ligand moieties.

The present invention, in another aspect thereof, relates to a dirhodium catalyst composition which includes a dirhodium tetracarboxylate catalyst and a solid support, and the dirhodium tetracarboxylate catalyst and the solid support are bound together.

The present invention, in yet another aspect thereof, relates to a dirhodium catalyst composition which includes a dirhodium catalyst and a solid support. The dirhodium catalyst includes a Rh—Rh moiety, and the dirhodium catalyst and the solid support are bound together via at least one of the rhodiums' axial positions.

As used herein, "alkyl" is meant to include linear alkyls, branched alkyls, and cycloalkyls, each of which can be substituted or unsubstituted. "Alkyl" is also meant to include lower linear alkyls (e.g., C1–C6 linear alkyls), such as methyl, ethyl, n-propyl, n-butyl, n-pentyl, and n-hexyl; lower branched alkyls (e.g., C3–C8 branched alkyls), such as isopropyl, t-butyl, 1-methylpropyl, 2-methylpropyl, 1-methylbutyl, 2-methylbutyl, 3-methylbutyl, 1,2-dimethylpropyl, 1,1-dimethylpropyl, 2,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 2-methyl-2-ethylpropyl, 2-methyl-l-ethylpropyl, and the like; and lower cycloalkyls (e.g., C3–C8 cycloalkyls), such as cyclopropyl, cyclobutyl, cyclopentyl, cyclohexyl, and the like. "Alkyl", as use herein, is meant to include unsubstituted alkyls, such as those set forth above, in which no atoms other than carbon and hydrogen are present. "Alkyl", as use herein, is also meant to include substituted alkyls. Suitable substituents include aryl groups (which may themselves be substituted), heterocyclic rings (saturated or unsaturated and optionally substituted), alkoxy groups (which is meant to include aryloxy groups (e.g., phenoxy groups)), amine groups (e.g., disubstituted with aryl or alkyl groups), carboxylic acid derivatives (e.g., carboxylic acid esters, amides, etc.), halogen atoms (e.g., Cl, Br, and I), and the like. Further, alkyl groups bearing one or more alkenyl or alkynyl substituents (e.g., a methyl group itself substituted with a prop-1-en-1-yl group to produce a but-2-en-1-yl substituent) is meant to be included in the meaning of "alkyl".

As used herein, "alkoxy" is meant to include groups having the formula —O—R, where R is an alkyl or aryl group. They include methoxy, ethoxy, propoxy, phenoxy, 4-methylphenoxy, and the like.

As used herein, "aryl" is meant to include aromatic rings, for example, aromatic rings having from 4 to 12 members, such as phenyl rings. These aromatic rings can optionally contain one or more heteroatoms (e.g., one or more of N, O, and S), and, thus, "aryl", as used herein, is meant to include heteroaryl moieties, such as pyridyl rings and furanyl rings. The aromatic rings can be optionally substituted. "Aryl" is also meant to include aromatic rings to which are fused one or more other aryl rings or non-aryl rings. For example, naphthyl groups, indole groups, and 5,6,7,8-tetrahydro-2-naphthyl groups (each of which can be optionally substituted) are aryl groups for the purposes of the present application. As indicated above, the aryl rings can be optionally substituted. Suitable substituents include alkyl groups (which can optionally be substituted), other aryl groups (which may themselves be substituted), heterocyclic rings (saturated or unsaturated), alkoxy groups (which is meant to include aryloxy groups (e.g., phenoxy groups)), amine groups (e.g., disubstituted with aryl or alkyl groups), carboxylic acid groups, carboxylic acid derivatives (e.g., carboxylic acid esters, amides, etc.), halogen atoms (e.g., Cl, Br, and I), and the like As used herein, "ring" refers to a homocyclic or heterocyclic ring which can be saturated or unsaturated. The ring can be unsubstituted, or it can be substituted with one or more substituents. The substituents can be saturated or unsaturated, aromatic or nonaromatic, and examples of suitable substituents include those recited above in the discussion relating to substituents on alkyl and aryl groups. Furthermore, two or more ring substituents can combine to form another ring, so that "ring", as used herein, is meant to include fused ring systems. In the case where the ring is saturated (i.e., in the case where each of the atoms making up the ring are joined by single bonds to other members of the ring), the ring may optionally include unsaturated (aromatic or nonaromatic) or saturated substituents.

As used herein, "solid support" is meant to include any material which can be bonded to the dirhodium catalyst and which can be separated from a liquid or solution, such as by filtration, centrifugation, decantation, and/or combinations thereof.

The solid support can be uniform through its thickness or it can be coated on a substrate (e.g., an inert substrate), such as on a stainless steel, glass, or other types of rod; stainless steel, glass, or other types of beads; the interior walls of reaction vessels, or a portion thereof; and the like.

A variety of solid supports can be used in the practice of the present invention.

For example, the solid support can be one which includes a nitrogen-containing heterocyclic pendant group. In this regard, suitable nitrogen-containing heterocyclic pendant groups include, for example, pyridyl groups, quinolinyl groups, isoquinolinyl groups, imidazolyl groups, benzimidazolyl groups, and the like. Illustratively, the pendant group can be bound to a polymeric solid support by conventional polymer chemistry to produce the desired solid support. How the pendant group is bonded into the solid support is not particularly critical to the practice of the present invention. Covalent bonding of the pendant group into a polymeric solid support is illustrative.

In one illustrative embodiment of the present invention, the solid support is a macroporous solid support; or it is a cross-linked polystyrene resin; or it is both.

As used herein, "macroporous solid support" is meant to include solid supports which have a porosity (e.g., pore size) substantially the same as the porosity of Argopore-Wang Resin. For purposes of the present invention, Resin A is to be deemed as having substantially the same as the porosity as Resin B if the ratio of the the average pore size of Resin A to the average pore size of Resin B is between about 0.5 and about 1.5, such as between about 0.6 and about 1.4, between about 0.7 and about 1.3, between about 0.8 and about 1.2, between about 0.9 and about 1.1, and/or between about 0.95 and about 1.05.

Suitable cross-linked polystyrene resins (whether macroporous or not) include those which are more highly cross-linked than a 1% cross-linked polystyrene resin. The degree of cross-linking can be ascertained by any conventional method known to those skilled in the art.

Additionally or alternatively, the solid support can be a cross-linked polystyrene resin (i.e., a cross-linked resin having a polystyrene backbone) which includes pendant groups having the formula:

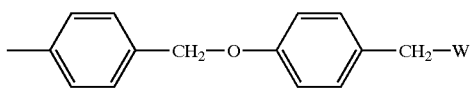

wherein W represents H, halogen, a hydroxy group, a thiol group, an alkoxy group, an alkylthio group, an aryl thio group, or combinations thereof. Illustratively, the cross-linked polystyrene resin can be one bearing pendant groups having the above formula in which W represents a —OW' group and in which W' is an aryl group, such as in the case where W' represents a substituted or unsubstituted phenyl group or a substituted or unsubstituted pyridyl group (e.g., a 4-pyridyl group). As further illustration of the variety of groups that can be used for W', W' can represent any nitrogen-containing heterocycle, for example, a pyridyl group (as mentioned above), a quinolinyl group, an isoquinolinyl group, an imidazolyl group, or a benzimidazolyl group.

Still other suitable solid supports are those having a polymer backbone (e.g., a cross-linked polystyrene resin) which includes pendant groups having the formula:

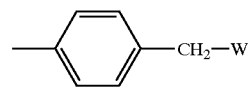

wherein W has the meaning set forth in the preceding paragraph.

A variety of other considerations can be taken into account when choosing a solid support. These include, for example, the propensity of the solid support to adhere to reaction vessels (glass, stainless steel, etc.); the effect of the length of a pendant group on possible steric interactions between the dirhodium catalyst and the polymer backbone; the compatibility of the solid support with various solvents to which it may be exposed; the solid support's swelling characteristics; and the like.

As used herein, "dirhodium catalyst" is meant to include any material which is, can be, or has been used as a catalyst and which contains two rhodium atoms and/or ions that are bonded with one another. The nature of the bond between the two rhodium atoms is not limitative: it can be covalent, ionic, van der Walls, pi-pi, sigma-pi, etc., or combinations of these. Of course, the dirhodium catalyst can include other atoms or ions or groups of atoms (e.g., ligands). Illustratively, each rhodium in the dirhodium catalyst can have a formal charge of +2, and the charge on the overall complex can be neutral.

Examples of "dirhodium catalysts" include catalysts having the formula $L_4Rh-RhL_4$ where each of the L's is the same or different and represents a coordinating atom from one or more ligands.

In certain aspects of the present invention, the dirhodium catalyst includes a Rh—Rh moiety and four bridging ligand moieties. As used herein, a "bridging ligand moiety" is meant to refer to a moiety which bridges between the two rhodium atoms. Suitable "bridging ligand moieties" include, for example, carboxylate moieties and amide moieties. For example, the dirhodium catalyst can include a Rh—Rh moiety and four bridging ligand moieties where each of the four bridging ligand moieties are independently selected from carboxylate moieties (each of which provides two coordinating oxygen atoms bonded to a single carbon atom) and amide moieties (each of which provides one coordinating oxygen atom and one coordinating nitrogen atom bonded to a single carbon atom). In this context, the dirhodium catalyst can be, for example, a dirhodium tetracarboxylate catalyst (i.e., a catalyst having the formula $L_4Rh-RhL_4$ where each of the L's represents a carboxylate oxygen from one of four carboxylate groups); a dirhodium tetracarboxamidate catalyst (i.e., a catalyst having the formula $L_4Rh-RhL_4$ where four of the L's represent a carbonyl oxygen from one of four amide groups and where the remaining four L's represent a nitrogen from one of four amide groups); a dirhodium tricarboxylate monocarboxamidate catalyst (i.e., a catalyst having the formula L$_4$Rh—RhL$_4$ where six of the L's each represent a carboxylate oxygen from one of three carboxylate groups, where one of the L's represents a carbonyl oxygen the amide group, and where the remaining L represents a nitrogen from the amide group); a dirhodium dicarboxylate dicarboxamidate catalyst (i.e., a catalyst having the formula L$_4$Rh—RhL$_4$ where four of the L's each represent a carboxylate oxygen from one of two carboxylate groups, where two of the L's each represent a carbonyl oxygen one of two amide groups, and where the remaining two L's each represent a nitrogen from one of two amide groups); or a dirhodium monocarboxylate tricarboxamidate catalyst (i.e., a catalyst having the formula L$_4$Rh—RhL$_4$ where two of the L's each represent a carboxylate oxygen from the carboxylate group, where three of the L's each represent a carbonyl oxygen from one of three amide groups, and where the remaining three L's each represent a nitrogen from one of three amide groups).

Examples of dirhodium tetracarboxylate catalysts include dirhodium acetate dimer, dirhodium propionate dimer, dirhodium butyrate dimer, dirhodium pentanoate dimer, dirhodium hexanoate dimer, dirhodium heptanoate dimer, dirhodium octanoate dimer, fluorinated analogs thereof (e.g. dirhodium heptafluorobutyrate dimer), and combinations thereof.

Other illustrative examples of dirhodium tetracarboxylate catalysts include those having the formula ("Formula I"):

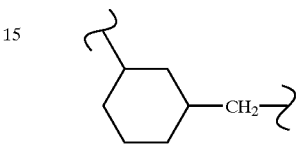

In Formula I, each of M$^1$ and M$^2$ is Rh. Z$^4$ represents the atoms necessary to complete a 3–12 membered heterocyclic ring, such as an alkylene moiety (e.g., a —CH$_2$CH$_2$CH$_2$- moiety). Q$^3$ is an electron withdrawing group, such as a group having the formulae —C(O)R$^9$, —SO$_2$R$^9$, or —P(O)R$^9$R$^{9'}$, where each of R$^9$ and R$^{9'}$ is independently selected from an alkyl group, an aryl group, and an alkoxy group.

As used herein, "electron withdrawing group" refers to those groups which are able to withdraw electron density from adjacent positions in a molecule, as determined, for example, by reference to the tables in the classical works which establish the classification of various substituents according to their electron withdrawing character. For example, reference may be made to the classification established by the Hammett scale, such as the one set forth in Gordon et al., *The Chemist's Companion*, New York: John Wiley & Sons, pp. 145–147 (1972) ("Gordon"), which is hereby incorporated by reference. Suitable electron-withdrawing groups include those having a para σ value higher than or equal to about 0.2 or higher than or equal to about 0.3, with reference to the Hammett scale. Particular examples of electron withdrawing groups are moieties having the formulae —C(O)R, —SO$_2$R, and —P(O)RR', where R and R' are independently selected from an alkyl group, an aryl group, and an alkoxy group.

As used herein, "alkylene" refers to a bivalent alkyl group, where alkyl has the meaning given above. Linear, branched, and cyclic alkylenes, as well as examples thereof, are defined in similar fashion with reference to their corresponding alkyl group. Examples of alkylenes include eth-1,1-diyl (i.e., —CH(CH$_3$)—), eth-1,2-diyl (i.e., —CH$_2$CH$_2$—), prop-1,1-diyl (i.e., —CH(CH$_2$CH$_3$)—), prop-1,2-diyl (i.e.,—CH$_2$—CH(CH$_3$)—), prop-1,3-diyl (i.e., —CH$_2$CH$_2$CH$_2$—), prop-2,2-diyl (e.g. —C(CH$_3$)$_2$—), cycloprop-1,1-diyl, cycloprop-1,2-diyl, cyclopent-1,1-diyl, cyclopent-1,2-diyl, cyclopent-1,3-diyl, cyclohex-1,1-diyl, cyclohex-1,2-diyl, cyclohex-1,3-diyl , cyclohex-1,4-diyl, but-2-en-1,1-diyl, cyclohex-1,3-diyl, but-2-en-1,4-diyl, but-2-en-1,2-diyl, but-2-en-1,3-diyl, but-2-en-2,3-diyl. Also included in the meaning of the term "alkylene" are compounds having the formula —R'—R"—, where —R' represents a linear or branched alkyl group and R"— represents a cycloalkyl group, such as moieties having the formula:

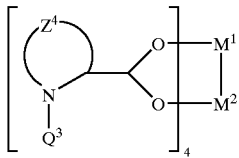

In Formula I and in all other formulae set forth in this document which contain one or more chiral centers and which do not specify the stereochemistry of a particular chiral center, such formulae are to be construed as encompassing all possible stereochemistries. Thus, for example, Formula I is meant to include (i) compounds in which the unspecified chiral center is entirely in the R configuration, (ii) compounds in which the unspecified chiral center is entirely in the S configuration, and (iii) racemic and other mixtures of (i) and (ii). Illustratively, dirhodium tetracarboxylate catalysts of Formula I are meant to include substantially chirally pure catalysts having one of the following formulae ("Formula II-A" and "Formula II-B", respectively):

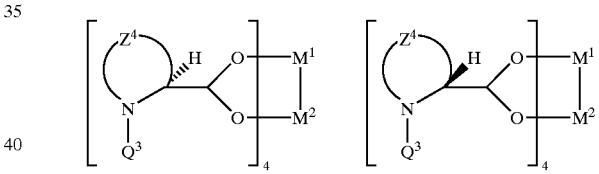

as well as dirhodium tetracarboxylate catalysts of Formula I having D$_2$ symmetry. Molecules having D$_2$ symmetry are molecules which have a vertical C$_2$ axis and a set of two C$_2$ axes perpendicular to the vertical C$_2$ axis. D$_2$ symmetry is further described in, for example, Cotton et al., *Advanced Inorganic Chemistry*, 4th ed., New York: John Wiley & Sons, pages 28–46 (1980), which is hereby incorporated by reference.

Specific examples of suitable catalysts having Formulae I and II include: Rh$_2$(DOSP)$_4$, Rh$_2$(S-DOSP)$_4$, and Rh$_2$(R-DOSP)$_4$, which are compounds having Formulae I, II-A, and II-B, respectively, in which each of M$^1$ and M$^2$ is Rh, Z$^4$ is a —CH$_2$CH$_2$CH$_2$— group, and Q$^3$ represents a 4-dodecylphenylsulfonyl moiety; and Rh$_2$(TBSP)$_4$, Rh$_2$(S-TBSP)$_4$, and Rh$_2$(R-TBSP)$_4$, which are compounds having Formulae I, II-A, and II-B, respectively, in which each of M$^1$ and M$^2$ is Rh, Z$^4$ is a —CH$_2$CH$_2$CH$_2$— group, and Q$^3$ represents a 4-t-butylphenylsulfonyl moiety. These and other illustrative compounds having Formulae I, II-A, and II-B are described in greater detail in Davies, "Rhodium-Stabilized Vinylcarbenoid Intermediates in Organic Synthesis," *Current Organic Chemistry*, 2:463–488 (1998), which is hereby incorporated by reference.

Other suitable dirhodium tetracarboxylate catalysts include those which contain two rhodium atoms or ions that are bonded to one another along an axis. This can be represented by the formula Rh—Rh, where the dash represents the Rh-to-Rh bond and the bond axis. These catalysts also contain two carboxylate ligands. As used herein, "carboxylate ligands" means ligands which contain one or more carboxylate groups. As used herein, carboxylate groups mean groups having the formula:

which can be written with the following formula:

where the dashed line represents the delocalized electrons. Alternatively, the carboxylate group can be expressed without showing the delocalized electrons, as in the following formula:

Each of the two carboxylate ligands includes two carboxylate groups, and these two carboxylate groups are bonded to each other via a moiety having the formula ("Formula III"):

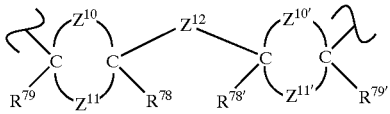

In Formula III, $Z^{10}$ and $Z^{11}$, together with the atoms to which they are bonded form a 3–12 membered ring, and $Z^{10'}$ and $Z^{11'}$, together with the atoms to which they are bonded form a 3–12 membered ring. $Z^{10}$ and $Z^{10'}$ can be the same, and each can contain a heteroatom, such as a nitrogen, oxygen, or sulfur. For example in one embodiment, $Z^{10}$ and $Z^{10'}$ are the same, and each represents a single heteroatom selected from the group consisting a sulfur atom, an oxygen atom, and an optionally substituted nitrogen atom. In another illustrative embodiment, at least one of $Z^{10}$ and $Z^{10'}$ has the formula —NQ—, at least one of $Z^{11}$ and $Z^{11'}$ is an arylene or alkylene group, and Q is an electron withdrawing group. In yet another illustrative embodiment, each of $Z^{10}$ and $Z^{10'}$ has the formula —NQ—, each of $Z^{11}$ and $Z^{11'}$ is an alkylene group, and Q is an electron withdrawing group. Although one of $Z^{10}$ and $Z^{11}$ and/or one of $Z^{10'}$ and $Z^{11'}$ can represent a direct bond between the carbons to which they are attached, this need not be the case, for example as when only three, only two, only one, or none of $Z^{10}$, $Z^{11}$, $Z^{10'}$, and $Z^{11'}$ represents such a direct bond. $R^{78}$, $R^{78'}$, $R^{79}$, and $R^{79'}$ are independently selected from the group consisting of H, an alkyl group, and an aryl group, such as in the case where each of $R^{78}$, $R^{78'}$, $R^{79}$, and $R^{79'}$ represents a hydrogen. $Z^{12}$ represents an alkylene or arylene group, such as a substituted or unsubstituted 1,3-phenylene group.

As indicated in the formulae above, each of the two carboxylate groups includes a first carboxylate oxygen atom ("$O^1$"), a second carboxylate oxygen atom ("$O^2$"), and a carbon ("C") to which the $O^1$ and the $O^2$ are bonded thereby forming two $O^1$—C—$O^2$ moieties. $O^1$ of each of the two carboxylate groups of each of the two carboxylate ligands is bonded to the first rhodium ($Rh^1$); $O^2$ of each of the two carboxylate groups of each of the two carboxylate ligands is bonded to the second rhodium ($Rh^2$).

Each of the two carboxylate ligands further includes at least two stereocenters. These stereocenters, for example, can be included in one or more of $Z^{10}$, $Z^{11}$, $Z^{10'}$, and $Z^{11'}$, and/or they can be located at the carbon atoms to which $Z^{10}$, $Z^{11}$, $Z^{10'}$, and $Z^{11'}$ are bonded. The stereochemistry at these stereocenters are selected such that the catalyst, taken as a whole, has $D_2$ symmetry.

Illustrative examples of such dirhodium tetracarboxylate catalysts include those having the formula ("Formula IV"):

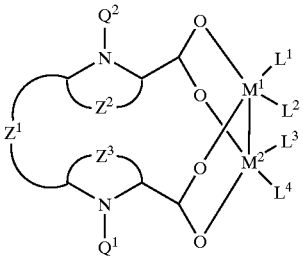

In Formula IV, $M^1$ and $M^2$ represent rhodium atoms or ions. $Z^2$ and $Z^3$, independently, are the atoms necessary to complete a 3–12 membered heterocyclic ring. Examples of such atoms include, for example: substituted or unsubstituted alkylene moieties, such as those having the formula —$(CH_2)_i$—, where i is an integer from 1 to 8; and moieties having the formula —$(CH_2)_i$—X—$(CH_2)_j$—, where i and j each independently represent integers from 0 to 4 and X is a heteroatom, such as O, S, and $NR^{70}$, where $R^{70}$ is a substituted or unsubstituted alkyl, aryl, or heteroaryl group. Illustratively, $Z^2$ and $Z^3$ can be the same, as in the case where each of $Z^2$ and $Z^3$ has the formula —$CH_2CH_2$—. $Z^1$ is an alkylene or arylene group. Illustratively, $Z^1$ can have the formula —$(CH_2)_i$—, where i is an integer from 1 to 8. Alternatively, $Z^1$ can have the formula —$(CH_2)_i$—X—$(CH_2)_j$—, where i and j each independently represent integers from 0 to 4 and X is a heteroatom, such as O, S, and $NR^{70}$, where $R^{70}$ is an alkyl or aryl group. Still alternatively, $Z^1$ can be a cycloalkyl moiety, such as cyclopent-1,3-diyl and cyclohex-1,3-diyl, which can be substituted or unsubstituted. Still alternatively, $Z^1$ can be an arylene moiety, such as a 1,3-phenylene or 1,3-naphthylene, or an heterocyclic moiety, such as a pyrid-3,5-diyl, pyrid-2,6-diyl, 2H-pyran-3,5-diyl, and tetrohydropyran-3,5-diyl moiety. $Q^1$ and $Q^2$ are the same or different and are electron withdrawing groups. Examples of $Q^1$ suitable for use in the practice of the present invention are moieties having the formulae —$C(O)R^1$, —$SO_2R^1$, and —$P(O)R^1R^{1'}$, and examples of suitable $Q^2$ include moieties having the formulae —$C(O)R^2$, —$SO_2R^2$, and —$P(O)R^2R^{2'}$. In these formulae, each of $R^1$, $R^{1'}$, $R^2$, and $R^{2'}$ is independently selected from an alkyl group, an aryl group, and an alkoxy group. In one illustrative embodiment, $Q^1$ has the formula —$SO_2R^1$; $Q^2$ has the formula —$SO_2R^2$; and $R^1$ and $R^2$ are the same or different and are substituted or unsubstituted alkyl or aryl groups, such as in the case where $Q^1$ has the formula —$SO_2R^1$; $Q^2$ has the formula —$SO_2R^2$; and each of $R^1$ and $R^2$ is independently selected from the group consisting of 4-(t-butyl)phenyl, 2,4,6-trimethylphenyl, and 2,4,6-triisopropylphenyl. In the above Formula IV, $L^1$ and $L^3$, taken together, represent a —O—$CR^{13}$—O— moiety, and $L^2$ and $L^4$, taken together, represent a —O—$CR^{14}$—O— moiety. In these moieties, $R^{13}$ and $R^{14}$ can be the same or they can be different, and each is independently selected from the group consisting of alkyl groups and aryl groups. Alternatively, $R^{13}$ and $R^{14}$ can represent alkylene or arylene groups that are directly or indirectly bonded to one another. In the latter case, the dirhodium tetracarboxylate catalysts of Formula IV can be expressed as the following formula ("Formula V"):

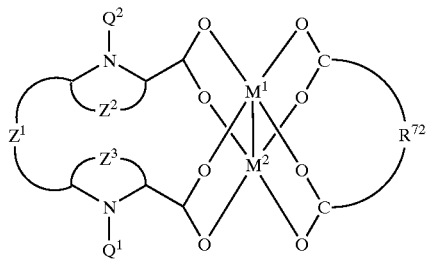

where $R^{72}$ represents an alkylene or arylene group. Illustratively, $R^{72}$ can be selected such that the dirhodium tetracarboxylate catalysts of Formula V have the following formula ("Formula VI"):

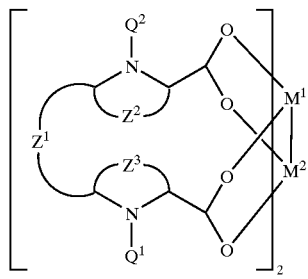

The dirhodium tetracarboxylate catalysts of Formulae IV, V, and VI have at least four stereocenters (i.e., at least the two carbons to which $Z^2$ is bonded and at least the two carbons to which $Z^3$ is bonded are stereocenters). Formulae IV, V, and VI are not meant to be limited to any particular set of configurations at the catalyst's stereocenters, and the structures given in these formulae are meant to be broadly read to include any and all possible collections of stereocenters. For example, catalysts of Formula VI are meant to include (i) compounds having the formula ("Formula VII"):

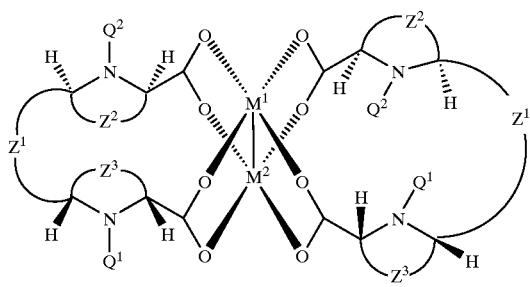

and (ii) compounds having the formula ("Formula VIII"):

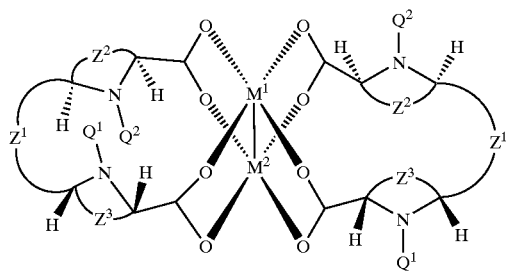

Each of the catalysts having Formulae VII and VIII can be present alone (i.e., as a pure diastereoisomer), or it can be present in a mixture with one or more different diastereoisomers. Alternatively, the catalysts having Formulae VII and VIII can be substantially free of other diastereoisomers. In this context, "substantially free of other disatereoisomers" means that the molar ratio of other diastereoisomers to the catalyst is less than 40%, such as less than 30%, less than 20%, less than 10%, less than 5%, less than 2%, and/or less than 1%.

Examples of catalysts having Formula VII and VIII, respectively, are those having the formula ("Formula IX"):

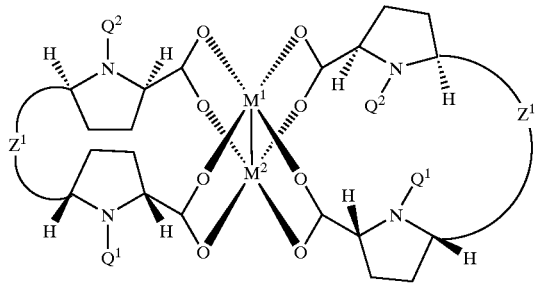

and those having the formula ("Formula X"):

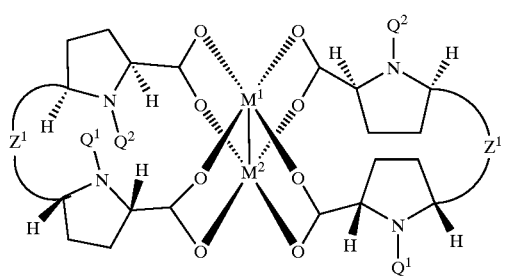

Still other examples of catalysts having Formula VII and VIII, respectively, are those having the formula ("Formula XI"):

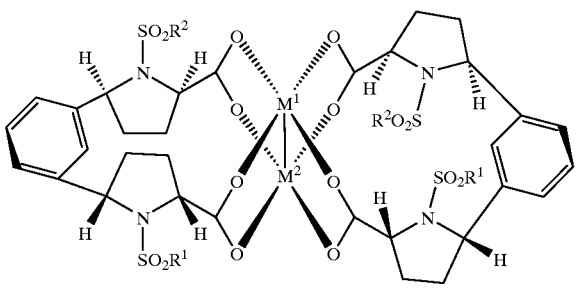

and those having the formula ("Formula XII"):

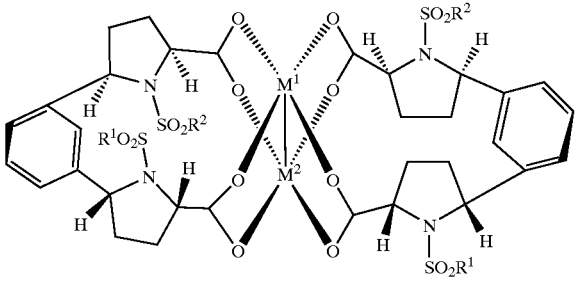

In Formula XI and Formula XII, $R^1$ and $R^2$ can be the same or different and each can be selected from, for example, alkyl groups and aryl groups.

As used in the above discussion and elsewhere herein, "arylene" is meant to include a bivalent aryl group in which both valencies are present on aromatic carbons. Examples of such groups include, for example, 1,3-phenylene, 1,4-phenylene, 5-methyl-1,3-phenylene, pyrid-2,3-diyl, pyrid-2,4-diyl, pyrid-2,5-diyl, pyrid-3,5-diyl, 1,3-naphthylene, 1,7-naphthylene, 1,8-naphthylene, 5,6,7,8-tetrahydro-1,3-naphthylene, thiophene-2,5-diyl, and furan-2,5-diyl. "Arylene", as used herein, is also meant to include a bivalent group having the formula —R—R'—, where R is an alkyl group and R' is an aryl group. As the structure of —R—R'— indicates, one of the valencies is on the R (i.e., alkyl) portion of the —R—R'— moiety and the other of the valencies resides on the R' (i.e., aryl) portion of the —R—R'— moiety. Examples of this type of arylene moiety include moieties having the formulae:

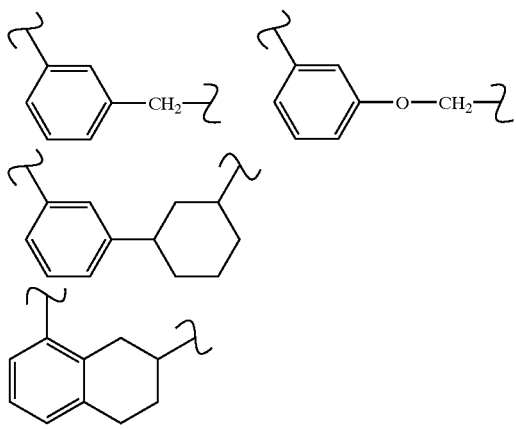

and the like.

Other suitable dirhodium tetracarboxylate catalysts as well as methods for making various dirhodium tetracarboxy-late catalysts are described in, for example, U.S. Pat. No. 6,410,746 to Davies; International Publication No. WO 00/64583; and Davies et al., "Novel Dirhodium Tetraprolinate Catalysts Containing Bridging Prolinate Ligands For Asymmetric Carbenoid Reactions," *Tetrahedron Letters*, pages 5287–5290 (1999), each of which is hereby incorporated by reference.

Other suitable dirhodium tetracarboxylate catalysts include dirhodium tetracarboxamidate catalysts, such as those having the following formula ("Formula XIII"):

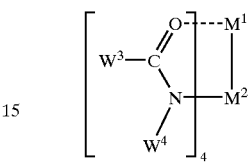

In Formula XIII, each of $M^1$ and $M^2$ is Rh. $W^3$ represents an alkyl group, an aryl group, an alkoxy group, or an amine group, and $W^4$ represents an alkyl group or an aryl group. Alternatively, $W^3$ and $W^4$, taken together with the atoms to which they are bonded, represent a 3–12 membered ring, for example, as shown in the following formula ("Formula XIV"):

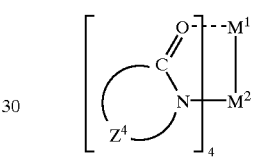

In Formula XIV, $Z^4$ represents the atoms necessary to complete a 3–12 membered ring. The ring can be substituted or unsubstituted; and it can include additional heteroatoms (i.e., in addition to the N to which $Z^4$ is bonded, or it can consist only of carbons (except for the N to which $Z^4$ is bonded). Illustratively, $Z^4$, together with the carbon and N atoms to which it is bonded, can represents a substituted or unsubstituted C3–C8 lactam ring, a substituted or unsubstituted oxazolidone ring, a substituted or unsubstituted pyrrolidone ring, or a substituted or unsubstituted imidazolidone ring. Specific examples of suitable catalysts of Formula XIV include: dirhodium(II) tetrakis(caprolactam); dirhodium(II) tetrakis[methyl 2-oxazolidone-4-carboxylate]; dirhodium(II) tetrakis[methyl 2-oxazolidone-4-(S)-carboxylate]; dirhodium(II) tetrakis[methyl 2-pyrrolidone-5-carboxylate]; dirhodium(II) tetrakis[methyl 2-pyrrolidone-5(R)-carboxylate]; dirhodium(II) tetrakis [methyl 2-pyrrolidone-5(S)-carboxylate]; dirhodium(II) tetrakis[methyl 1-(3-phenylpropanoyl)-2-imidazolidone-4-carboxylate; dirhodium(II) tetrakis[methyl 1-(3-phenylpropanoyl)-2-imidazolidone-4(S)-carboxylate; and adducts (e.g., acetonitrile and/or alcohol adducts) thereof. Methods for producing these and other dirhodium tetracarboxamidate catalysts can be found, for example, in U.S. Pat. No. 5,175,311 to Doyle, which is hereby incorporated by reference.

As indicated above, in the dirhodium catalyst compositions of the present invention, the dirhodium catalyst and the solid support are bound together. As used herein, "bind" or "bound" is meant to refer to any form of attachment, including, for example, covalent, ionic, van der Walls, pi-pi, sigma-pi, etc. or combinations of these forms of attachment. As used herein, "bind" or "bound" is also meant to refer to mechanical forms of attachment, where, for example, binding occurs primarily via mechanical sequestration and/or encapsulation (e.g., where one compound is trapped in a pore of another material). As used herein, "bind" or "bound" is also meant to refer to forms of attachment in which the product of binding is thermodynamically stable or in which the product of binding is thermodynamically unstable but which is stabilized kinetically.

In certain aspects of the present invention, the dirhodium catalyst and the solid support are bound together, but they are not covalently bound together via one or more of the ligand moieties. With regard to such aspects of the present invention, the dirhodium catalyst and the solid support are to be deemed to be "not covalently bound together via one or more of the ligand moieties" if and only if none of the ligand moieties are connected to the solid support (i) via a covalent bond or (ii) via a series of bonds, all of which are covalent. In this context, a bond is to be deemed to be covalent if and only if it involves the sharing of electrons, such as in the case where the bond is a carbon/carbon bond, a carbon/oxygen bond, a carbon/nitrogen bond, and the like.

In other certain aspects of the present invention, the dirhodium catalyst and the solid support are bound together via at least one of the rhodiums' axial positions. With regard to such aspects of the present invention, the dirhodium catalyst and the solid support are to be deemed to be "bound together via at least one of the rhodiums' axial positions" if and only if there is a bond between an axial position of one of the rhodium atoms and one of the atoms of the solid support. As is implicit in all of the above discussion, atoms of pendant groups which are bound directly or indirectly to the solid support infrastructure (e.g., a polymer backbone) are, for the purposes of the present invention, considered to be "atoms of the solid support". Furthermore, as used herein, a rhodium's axial position is meant to refer to the position which is substantially in line with the Rh—Rh bond (as distinguished, for example, from the rhodium's equatorial positions).

The dirhodium catalyst compositions described above can be produced by a variety of methods.

For example, dirhodium catalyst compositions of the present invention can be produced by providing a dirhodium catalyst and contacting the dirhodium catalyst with a solid support under conditions effective to bind the dirhodium catalyst and the solid support together and to produce the dirhodium catalyst composition.

The dirhodium catalyst which is employed in this method can be purchased commercially, or it can be prepared using any suitable method, such as those described in U.S. Pat. No. 6,410,746 to Davies; U.S. Pat. No. 5,175,311 to Doyle; International Publication No. WO 00/64583; and Davies et al., "Novel Dirhodium Tetraprolinate Catalysts Containing Bridging Prolinate Ligands For Asymmetric Carbenoid Reactions," *Tetrahedron Letters*, pages 5287–5290 (1999), each of which is hereby incorporated by reference.

Suitable solid supports can be obtained commercially, or they can be prepared by methods well known to those skilled in the art. For example, in cases where polymeric solid supports bearing pendant groups are used, such solid supports can be obtained commercially, or they can be prepared using standard techniques for adding pending groups to polymeric backbones. Illustratively, starting with a polymer which includes pendant hydroxyl groups, the hydroxyl groups can be converted to bromides (e.g., using conventional triphenylphosphine/bromoform chemistry). The resulting bromide can be reacted with a suitable metal alkoxide (e.g., one having the formula D—OM", where M represents an alkali metal and D represents the pendant group to be incorporated into the solid support), such as sodium 4-pyridinylmethoxide or another alkali metal 4-pyridinylmethoxide. In cases where silica based solid supports (e.g., glass, ceramics, and the like) are employed, the silica material can be functionalized with reactive groups using conventional silane chemistry (e.g., using functional trialkoxysilanes), which can then be reacted with the desired pendant group. Alternatively, again in cases where silica based solid supports are employed, the pendant group can be introduced by direct attachment to the silica material, for example, by treating the silica material with a trialkoxysilane bearing the desired pendant group. In cases where the solid support is based on a perfluorinated polymer (e.g., PTFE), the perfluorinated polymer can be functionalized with reactive oxygen groups using plasma and corona discharge treatments, ion beam and electron beam bombardment, x-ray and gamma ray treatments, treatments involving sodium metal/ammonia, treatments involving sodium naphthalene in glycol ether, treatments involving radio frequency glow discharge, and the like, for example, as described in Lee et al., "Wet-process Surface Modification of Dielectric Polymers: Adhesion Enhancement and Metallization," *IBM J. Res. Develop.*, 38(4) (July 1994); Vargo et al., "Adhesive Electroless Metallization of Fluoropolymeric Substrates," *Science*, 262:1711–1712 (1993); Rye et al., "Synchrotron Radiation Studies of Poly (tetrafluoroethylene) Photochemistry," *Langmuir*, 6:142–146 (1990); Tan et al., "Investigation of Surface Chemistry of Teflon. 1. Effect of Low Energy Argon Ion Irradiation on Surface Structure," *Langmuir*, 9:740–748 (1993), U.S. Pat. No. 5,051,312 to Allmer, and U.S. Pat. Nos. 4,946,903, 5,266,309, and 5,627,079, each to Gardella Jr. et al., which are hereby incorporated by reference. Subsequent reaction of the functionalized perfluorinated polymer with a suitably functionalized compound bearing the desired pendant group can be used to complete the preparation of the solid support.

The aforementioned dirhodium catalysts and solid supports can be provided neat (i.e., in the absence substantially all other materials) or either the dirhodium catalyst or the solid support or both can be provided as a mixture with other materials, such as, for example, solvents, reactants, and the like. Where the dirhodium catalyst is provided in solution form, it can be provided in concentrated form (e.g., at a concentration greater than about 5 times the concentration at which they will be used in a catalytic reaction), or it can be provided in dilute form (e.g., at a concentration less than about 5 times the concentration at which they will be used in the catalytic reaction). Where solvents are employed, it is desirable that the solvent used to suspend the solid support and the solvent used to dissolve or suspend the dirhodium catalyst be miscible with one another or miscible with the solvent in which the catalytic reaction is to be carried out. The choice of solvent(s), of course, will depend on a number of factors including solubility of the solid support and/or dirhodium catalyst in the solvent(s); possible side reactions between the solvent(s) and the solid support, the dirhodium catalyst and other materials to be present during the catalytic reaction; difficulty of separating product from the solvent(s); difficulty in drying the solvent (in cases where dry solvent is needed); boiling point and/or decomposition point of the solvent relative to the temperature at which the catalytic is to be carried out; cost considerations; disposal considerations; and the like. Suitable solvents include, for example, hydrocarbon solvents (e.g., hexanes and cyclohexane) and chlorinated hydrocarbons (e.g., chloroform and methylene chloride), as well as aromatic solvents (e.g., toluene and xylenes).

Once the dirhodium catalyst and the solid support are provided, they are contacted with one another under conditions effective to bind the dirhodium catalyst and the solid support together and to produce the dirhodium catalyst composition. This contact can take place at any time prior to, during, or even subsequent to the catalytic reaction. Illustratively, the dirhodium catalyst and solid support can be contacted with one another prior to being mixed with the reactant(s) to be catalyzed. Alternatively, the dirhodium catalyst can be premixed with the reactant(s), and then this mixture can be contacted with the solid support. Still alternatively, the solid can be premixed with the reactant(s), and then this mixture can be contacted with the dirhodium catalyst. Still alternatively, the solid support can be premixed with a portion of the reactants, the dirhodium catalyst can be premixed with the remainder of the reactants, and then the two mixtures can be mixed together, thus contacting the dirhodium catalyst and solid support with one another.

It should be understood that where the present application recites a 2-step process of (i) providing a dirhodium catalyst composition containing dirhodium catalyst ("DC") bound together with a solid support ("SS") and (ii) contacting this composition with some other material ("OM"), such as a reactant, step (i) can be performed first (e.g., by mixing DC and SS with each other) and then, in a separate step (ii), contacting the resulting dirhodium catalyst composition with OM. Alternatively, steps (i) and (ii) can be performed simultaneously, for example, by first mixing DC and OM and then contacting the DC/OM mixture with SS; by first mixing SS and OM and then contacting the SS/OM mixture with DC; or by adding SS and DM separately but simultaneously to OM.

In one embodiment of the present invention, the dirhodium catalyst and the solid support are brought into contact with one another either prior to commencement of the reaction (e.g., prior to contacting the catalyst with the reactant(s)) or shortly after the reaction has begun (e.g., before more than half of the expected yield of product is produced). Although contacting the dirhodium catalyst and the solid support with one another late in the reaction (e.g., after more than half of the expected yield of product is produced) or after the reaction is complete or substantially complete (e.g., after more than 90% of the expected yield of product is produced), for example, by adding the solid support to the reaction mixture, may not be optimal, such a practice can, nevertheless, be effective, for example, in facilitating separation of the dirhodium catalyst from the reaction mixture.

Details with respect to the temperature at which contact takes place, the medium in which contact takes place, and the like do not appear to be particularly critical. Contacting the dirhodium catalyst and the solid support at room temperature in methylene chloride has proven to be suitable, although contact can be carried out at any temperature from the freezing point to the boiling point of the solvent.

As alluded to above, "dirhodium catalyst composition", as used herein, is meant to refer to the composition in combination with one or more other materials (e.g., in the presence of solvents, reactants and/or products involved in the reaction to be catalyzed), substrates to which the solid support may be bound, etc. However, it will be appreciated that, as used herein, "dirhodium catalyst composition" is also meant to refer to the composition alone (without any other materials being present), as in the case where the dirhodium catalyst composition is formed by contacting the dirhodium catalyst and solid support in the presence of a solvent followed by solvent removal (e.g., by evaporation, filtration, centifugation, and/or decantation) or as in the case where the dirhodium catalyst composition is separated from a reaction mixture subsequent to completion of the reaction. In one illustrative embodiment, the dirhodium catalyst composition is packed into a column, said column then being useful for carrying one or more of the reactions discussed below, for example, by passing the reactants through the column. After use in one such reaction, product, unused reactant, by-products, etc., can be washed from the column using suitable solvents or combinations of solvents, and the column can be reused for the same or a different reaction. Such columns can be of any suitable size. For example, micro columns containing the dirhodium catalyst composition can be used for running test reactions or for optimizing reaction conditions.

The dirhodium catalyst compositions of the present invention can be used in a variety of dirhodium catalyzed reactions. Briefly, these include: insertion reactions (which are meant to include C—H insertions, Si—H insertions, O—H insertions, and N—H insertions) cyclopropanation reactions, annulations (which are meant to include [3+2] annulations and [3+4] annulations), and ω,ω-diarylalkanoate synthesis. These reactions can be carried out under an inert atmosphere (e.g., argon gas) and/or in the presence of a suitable drying agent, such as molecular sieves, sodium sulfate, magnesium sulfate, calcium sulfate, and the like.

For example, the method and composition of the present invention can be used in a variety of insertion reactions. One such insertion reaction relates to a method for producing a compound having the formula ("Formula XV"):

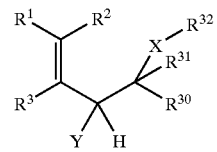

$R^1$, $R^2$, and $R^3$ are independently selected from H, alkyl, aryl, or vinyl, or $R^1$ and $R^3$, together with the atoms to which they are bonded, form a 5–12 membered ring, such as a cyclohexene ring, or a cyclohexa-1,3-diene ring. The method can be used to prepare compounds in which $R^1$ and $R^3$, together with the atoms to which they are bonded, form an aromatic ring, such as a substituted or unsubstituted phenyl ring, pyridine ring, thiophene ring, indole ring, etc. In the case where $R^1$ and $R^3$, together with the atoms to which they are bonded, form a phenyl ring, the compound produced by this method can have the formula ("Formula XVI"):

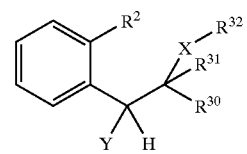

Y is an electron withdrawing group, examples of which include moieties having the formulae: —C(O)$R^{77}$, —SO$_2$$R^{77}$, and —P(O)$R^{77}R^{77'}$. In these formulae, each of $R^{77}$ and $R^{77'}$ is independently selected from an alkyl group, an aryl group, and an alkoxy group. Illustratively, Y can have the formula CO$_2$$R^{12}$ where $R^{12}$ is an alkyl group or an aryl group.

X is CH$_2$, O or NR$^{11}$, and $R^{11}$ is H, an alkyl group, an aryl group, an acyl group, an alkoxycarbonyl group, or a silyl group having the formula —SiR$^{33}$R$^{34}$R$^{35}$, where R$^{33}$, R$^{34}$, and R$^{35}$ are independently selected from an alkyl group and an aryl group.

Each of R$^{30}$ and R$^{31}$ is independently selected from the group consisting of H, alkyl, aryl, and vinyl. R$^{32}$ is an alkyl group, an aryl group, an acyl group, an alkoxycarbonyl group, or a silyl group having the formula —SiR$^{36}$R$^{37}$R$^{38}$, where R$^{36}$, R$^{37}$, and R$^{38}$ are independently selected from an alkyl group and an aryl group. Alternatively, R$^{31}$ and R$^{32}$, together with the atoms to which they are bonded, can form a 5–12 membered ring, such as a cyclopentyl or cyclohexyl ring (in the case where X is —CH$_2$), a piperidinyl ring (in the case where X is N), or a tetrahydrofuranyl or a tetrahydropyranyl ring (in the case where X is O). Illustratively, this method is well-suited for forming compounds having Formula XV in which X is not CH$_2$ when each of R$^{30}$ and R$^{31}$ is H.

The method includes providing a diazo compound having the formula ("Formula XVII"):

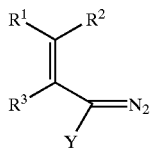

in which R$^1$, R$^2$, R$^3$, and Y have the same meanings as given above with reference to Formula XV. The method further includes converting the diazo compound with a compound having the formula ("Formula XVIII"):

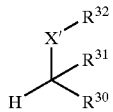

in the presence of a dirhodium catalyst composition of the present invention and under conditions effective to produce the compound. In compound XVIII, R$^{30}$, R$^{31}$, and R$^{32}$ are defined as they are above with regard to Formula XV. When, in the desired product, X is CH$_2$ or O, X' in Formula XVIII is CH$_2$ or O, respectively. When, in the desired product, X is NR$^{11}$, X' in Formula XVIII is NR$^{11'}$ and R$^{11'}$ is an alkyl group, an aryl group, an acyl group, an alkoxycarbonyl group (e.g., BOC or another alkoxycarbonyl amine protecting group), or a silyl group (e.g., a triarylsilyl group, or a trialkylsilyl group).

Suitable dirhodium catalysts for carrying out the conversion of XVII with XVIII are those having Formulae I–II and IV–XIV, as defined and discussed above. Other suitable dirhodium catalysts for carrying out the conversion of XVII with XVIII are chiral dirhodium catalysts, such as those having D$_2$ symmetry, for example, those which include a two rhodium atoms or ions that are bonded to one another along an axis and two carboxylate ligands, each of which two carboxylate ligands includes two carboxylate groups bonded to each other via a moiety having Formula III. Such dirhodium catalysts are discussed in greater detail above.

Illustratively, the reaction can be carried out by contacting the catalyst composition of the present invention with the compound of Formula XVIII. In the case where the compound of Formula XVIII is a liquid (e.g., in the case where the compound of Formula XVIII is tetrahydrofuran, tetrahydropyran, N-(tert-butyloxycarbonyl)pyrrolidine, N-(tert-butyloxycarbonyl)piperidine, cyclopentane, cyclohexane, etc.), this can be effected without the use of additional solvent. Alternatively, the mixture can be formed using an inert solvent or a solvent which is significantly less reactive toward the diazo compound of Formula XVII than is the compound of Formula XVIII. As an example, it has been found that when the compound of Formula XVIII is tetrahydrofuran, the catalyst composition can be contacted with neat tetrahydrofuran (i.e., using tetrahydrofuran as the solvent and without the use of additional solvent), or hexanes can be used as a reaction medium. The amount of catalyst used in this reaction can be about the same as the amount of catalyst which would be employed if the catalyst were not bound on a solid support. For example, suitable mole ratios of the catalyst to the diazo compound of Formula XVII are: from about 1:100,000 to about 1:20, such as from about 1:10,000 to about 1:50, from about 1:1000 to about 1:50, from about 1:500 to about 1:50, and/or from about 1:200 to about 1:100.

Once the catalyst composition is contacted with the compound of Formula XVIII, the diazo compound of Formula XVII is added, for example with stirring. This addition can be carried out in a single portion, continuously, or batchwise. Slow, dropwise addition can be effected, for example, using a syringe pump. The amount of diazo compound of Formula XVII added is generally dependent on the amount of the compound of Formula XVIII present in the reaction mixture. Illustratively, the mole ratio of the compound of Formula XVIII to the diazo compound of Formula XVII is from about 1:10 to about 10:1, such as from about 6:1 to about 1:1 and/or from about 4:1 to about 2:1. The addition can be carried out at any suitable temperature from the freezing point to the boiling point of the solvent and/or the compound of Formula XVIII. For example, the addition can be carried out from about −50° C. to about 60° C. Room temperature addition and addition at about 10° C. are illustrative. Illustratively, in one embodiment of the present invention where diastereomerically and/or enantiomerically pure product is desired, reaction conditions can be optimized by adjusting the addition temperature. Although not intending to be limitative in any way on the scope of the present invention, it is believed that (i) formation of diastereomerically and/or enantiomerically pure product can be favored by lower addition temperatures (e.g., from about −50° C. to about 10° C.); and (ii) yield and improved diastereoisomeric and/or enantiomeric purity can be improved by performing the reaction substantially in the absence of oxygen. As used herein, "substantially in the absence of oxygen" means that the liquid reactants and solvents (if any) employed in carrying out the reaction are degassed, for example by bubbling an inert gas (e.g., nitrogen or argon) therethrough, that the reaction is carried out under blanket of inert gas, and that all transfers (subsequent to degassing) are carried out such that ambient air is excluded (e.g., by using rubber septums, gas tight syringes, and the like).

The conversion of the compound of Formula XVII with a compound of Formula XVIII to produce either or both diastereomers of a compound of Formula XV described above can be used for preparing compounds having the formula ("Formula XIX"):

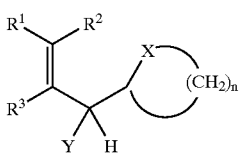

In this case, the conversion of the diazo compound of Formula XVII is carried out with a cyclic compound having the formula ("Formula XX"):

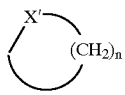

in which X' is defined as above and n is 3–10. In one illustrative embodiment, $R^1$ and $R^3$, together with the atoms to which they are bonded, form a phenyl ring, and Y has the formula —$CO_2R^{10}$ where $R^{10}$ is an alkyl or aryl group. The method can be used for making compounds in which X is $NR^{11}$ and in which n is 3 or 4. The method is also suitable for making compounds having the formulae ("Formula XXI-A" and "Formula XXI-B", respectively):

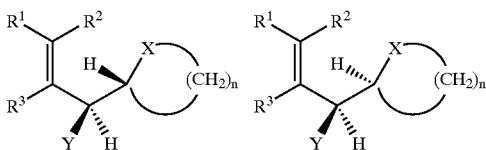

in which case the dirhodium catalyst employed is a chiral dirhodium catalyst. For example, by using the S-isomer of compounds having Formulae IV–XII, as defined and discussed above, compounds of Formula XXI-B which are substantially enantiomerically pure (e.g., >80% ee, >90% ee, >95% ee, >98% ee, and/or >99% ee) can be prepared. Examples of compounds having Formula XXI-A and XXI-B include those in which X is $NR^{11}$, n is 3 or 4, Y is $CO_2R^{12}$, $R^{12}$ is alkyl or aryl, and $R^1$ and $R^3$, together with the atoms to which they are bonded, form an aromatic ring, such as those compounds of Formulae XXI-A or XXI-B in which X is NH, $R^{12}$ is a methyl group, and $R^1$ and $R^3$, together with the atoms to which they are bonded, form a phenyl ring.

Such compounds can have one of the following formulae ("Formula XXII-A" and "Formula XXII-B", respectively):

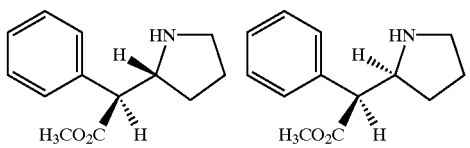

or one of the following formulae ("Formula XXII-C" and "Formula XXII-D", respectively):

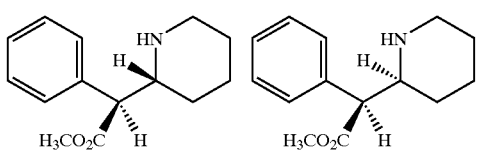

the latter of which is also referred to as threo methylphenidate and which is believed to be the biologically active form of RITALIN™. Where stereospecifcity is not important, racemic mixtures of compounds having Formulae IV–XII or other dirhodium tetracarboxylates can be employed in the method and/or composition of the present invention to produce the racemic methylphenidate.

The method of the present invention can also be used to prepare compounds having Formula XV in which X is $NR^{11}$ and in which $R^{31}$ and $R^{32}$, together with the atoms to which they are bonded, represent a ring having the formula ("Formula XXIII"):

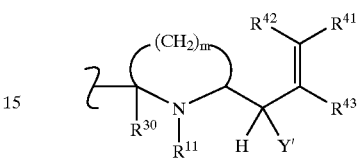

where $R^{30}$ is H. That is, the method can be used to prepare compounds having the formula ("Formula XXIV"):

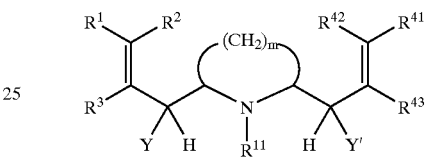

In these formulae, $R^{41}$, $R^{42}$, and $R^{43}$ are independently selected from H, alkyl, aryl, or vinyl, or $R^{41}$ and $R^{43}$, together with the atoms to which they are bonded, form a 5–12 membered ring. Y' is an electron withdrawing group, for example, the electron withdrawing groups discussed above with regard to Y, and m is 2–9. The reaction involves providing a diazo compound having Formula XVII and converting the diazo compound with a cyclic amine having the formula ("Formula XXV"):

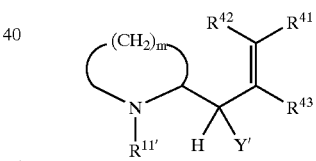

in the presence of a dirhodium catalyst composition of the present invention and under conditions effective to produce the compound. Suitable conditions for this reaction are the same as the ones discussed above with regard to the conversion of compounds of Formula XVII with compounds of Formula XVIII. By using a chiral catalyst, compounds having the formula ("Formula XXVI"):

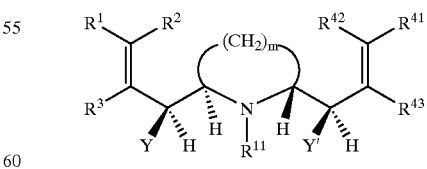

can be produced.

A variety of methods can be used to prepare the cyclic amine having Formula XXV, such as the method that is described above with regard to preparing compounds having Formula XIX using diazo compounds of Formula XVII, cyclic compounds of Formula XX, and a dirhodium catalyst composition of the present invention. Rather than running the reaction in two steps (i.e., by first reacting a diazo compounds of Formula XVII with a cyclic compound of Formula XX in which X is N to produce a cyclic amine having Formula XIX and then reacting the cyclic amine having Formula XIX with a diazo compound having Formula XVII to produce the desired compound of Formula XXIV), the reaction can be carried out in a single step by, for example, by contacting the cyclic compound of Formula XX in which X is N with at least two equivalents of a diazo compound of Formula XVII. Reaction conditions suitable for carrying out this one step reaction include those discussed above with regard to the two step method. Illustratively, during the first part of the reaction (i.e., during the addition of the first half of the diazo compound having Formula XVII), the reaction is carried out with cooling (e.g., from about −50° C. to about 0° C.). Then the reaction mixture is warmed, and the second part of the reaction (i.e., during the addition of the second half of the diazo compound having Formula XVII) is carried out at elevated temperatures (e.g., from about 20° C. to about 100° C.). Alkanes having melting points of less than about −50° C. and boiling points greater than about 60° C. are the suitable solvents for this reaction, but the nature of the solvent is not particularly critical and alternatives can be used.

The compounds prepared by the above method (i.e., compounds having Formulae XV, XVI, XIX, XXI-A, XXI-B, XXII-A, XXII-B, XXII-C, XXII-D, XXIV, and XXVI) are appropriately functionalized for further conversion by, for example, ester reduction or Grignard addition to highly functionalized bases. In the case where a chiral catalyst is employed, e.g., the S-isomer of compounds having Formulae IV–XII, as defined and discussed above, these compounds can be used as $C_2$ symmetric bases, or, as indicated above, they can be further converted (e.g., by ester reduction or Grignard addition) to highly functionalized $C_2$ bases. $C_2$ bases are very useful for controlling stereochemistry in organic synthesis, for example, as described in Takahata et al., "New Entry to C2 Symmetric Trans-2,6-bis (hydroxymethyl)piperidine Derivatives Via the Sharpless Asymmetric Dihydroxylation," *Tetrahedron-Asymmetry*, 6:1085–1088 (1995) and in Bennani et al., "Trans-1,2-diaminocyclohexane Derivatives as Chiral Reagents, Scaffolds, and Ligands for Catalysis—Applications in Asymmetric Synthesis and Molecular Recognition," *Chemical Reviews*, 97:3161–3195 (1997), which are hereby incorporated by reference.

Further examples and details of using dirhodium catalysts to effect insertions can be found, for example, in Davies et al., "Catalytic Asymmetric C—H Activation of Silyl Enol Ethers as an Equivalent of an Asymmetric Michael Reaction," *J. Am. Chem. Soc.*, 123(9):2070–2071 (2001); Davies et al., "Kinetic Resolution and Double Stereodifferentiation in Catalytic Asymmetric C—H Activation of 2-Substituted Pyrrolidines," *Organic Letters*, 3(11): 1773–1775 (2001); Davies et al., "Asymmetric Intramolecular C—H Insertions of Aryldiazoacetates," *Organic Letters*, 3(10):1475–1477 (2001); Catalytic Asymmetric C—H Activation of Alkanes and Tetrahydrofuran," *J. Am. Chem. Soc.*, 122(13):3063–3070 (2000); Davies et al., "Highly Regio-, Diastereo-, and Enantioselective C—H Insertions of Methyl Aryldiazoacetates into Cyclic N-Boc—Protected Amines. Asymmetric Synthesis of Novel $C_2$-Symmetric Amines and threo-Methylphenidate," *J. Am. Chem Soc.*, 121(27): 6509–6510 (1999); Davies et al., "Catalytic Asymmetric Synthesis of Syn-Aldol Products from Intermolecular C—H Insertions Between Allyl Silyl Ethers and Methyl Aryldiazoacetates," *Organic Letters*, 1(3):383–385 (1999); Davies, "Rhodium—Stabilized Vinylcarbenoid Intermediates in Organic Synthesis," *Current Organic Chemistry*, 2:463–488 (1998); Davies et al., "Recent Progress in Asymmetric Intermolecular C—H Activation by Rhodium Carbenoid Intermediates," *Journal of Organometallic Chemistry*, 617-618:47–55 (2001); Davies, "Dirhodium Tetra(N-arylsulfonylprolinates) as Chiral Catalysts For Asymmetric Transformations of Vinyl- and Aryldiazoacetates," *Eur. J. Org. Chem.*, pages 2459–2469 (1999); Davies, "Asymmetric Synthesis Using Rhodium-Stabilized Vinylcarbenoid Intermediates," *Aldrichimica Acta*, 30(4):107–114 (1997); U.S. Pat. No. 6,410,746 to Davies; and International Publication No. WO 00/64583. Collectively, these references are referred to herein as the "Insertion References", and each of these references is hereby incorporated by reference. The reactions set forth in the Insertion References and other references relating to dirhodium catalyzed insertion reactions can be carried out using the dirhodium catalyst composition of the present invention in place of the dirhodium catalysts described in the Insertion References. The amount and type of catalyst used in this reaction can be about the same as the amount and type of catalyst which would be employed if the catalyst were not bound on a solid support. Suitable types and amounts of catalyst include those specified hereinabove.

The method and composition of the present invention can also be used in connection with other insertion reactions, as well as with cyclopropanation reactions. Such other insertion reactions and such cyclopropanation reactions are illustrated by the following method for producing a compound having the formula ("Formula XXVII"):

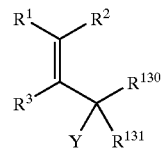

In Formula XXVII, $R^1$, $R^2$, and $R^3$ are independently selected from H, alkyl, aryl, or vinyl, or $R^1$ and $R^3$, together with the atoms to which they are bonded, form a 5–12 membered ring. Y is an electron withdrawing group (e.g., an ester group). $R^{131}$ is H, and $R^{130}$ is an alkyl group, an aryl group, an alkoxy group, an amine group, or a silyl group; or $R^{130}$ and $R^{131}$, together with the atom to which they are bonded, form a substituted or unsubstituted cyclopropane moiety. The method includes providing a diazo compound having the formula ("Formula XXVIII"):

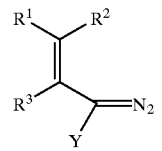

(in which $R^1$, $R^2$, $R^3$, and Y are defined as they are above with regard to Formula XXVII) and converting the diazo compound of Formula XXVIII to the compound of Formula XXVII in the presence of a dirhodium catalyst composition of the present invention and under conditions effective to produce the compound of Formula XXVII.

In cases where $R^{131}$ is H, and $R^{130}$ is an alkyl group, an aryl group, an alkoxy group, an amine group, or a silyl group, this reaction is a C—H, C—O, C—N, or C—Si insertion, and suitable reactants for effecting the conversion of the diazo compound of Formula XXVIII to the compound of Formula XXVII can be readily ascertained by one skilled in the art. Examples of such reactions are set forth in the Insertion References, and each of these references is hereby incorporated by reference. The reactions set forth in the Insertion References and other references relating to dirhodium catalyzed insertion reactions can be carried out using the dirhodium catalyst composition of the present invention in place of the dirhodium catalysts described in the Insertion References. To carry out the C—H, C—O, C—N, or C—Si insertion reactions represented by the conversion of the diazo compound of Formula XXVIII to the compound of Formula XXVII, the amount of catalyst can be about the same as the amount of catalyst which would be employed if the catalyst were not bound on a solid support. For example, suitable mole ratios of the catalyst to the diazo compound of Formula XXVIII are from about 1:100,000 to about 1:20, such as from about 1:10,000 to about 1:50, from about 1:1000 to about 1:50, from about 1:500 to about 1:50, and/or from about 1:200 to about 1:100.

The above-described insertion reactions exemplify the present invention's usefulness in catalyzing aryldiazomethane or vinyldiazomethane insertion reactions in which aryldiazomethanes or vinyldiazomethanes are contacted with a dirhodium catalyst composition according to the present invention under conditions effective to catalyze the aryldiazomethane or vinyldiazomethane insertion reaction. These methods provide new and useful ways to make compounds (such as the compounds illustrated by Formulae XV, XVI, XIX, XXI-A, XXI-B, XXII-A, XXII-B, XXII-C, XXII-D, XXIV, XXVI, and XXVII (in cases where $R^{131}$ is H)) and to produce C—H bonds.

In cases where $R^{130}$ and $R^{131}$, together with the atom to which they are bonded, form a substituted or unsubstituted cyclopropane moiety, the compound of Formula XXVII can have the formula ("Formula XXIX"):

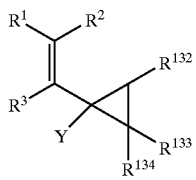

Such reactions are commonly referred to as cyclopropanation reactions. In Formula XXIX, each of $R^{132}$, $R^{133}$, and $R^{134}$ can independently represent H, an alkyl group, an aryl group, a silyloxy group, an alkoxy group, a halogen, an amine group, or an alkyl or aryl thiol group. Alternatively, $R^{132}$ and $R^{133}$, together with the atoms to which they are bonded, can form a 4–12 membered ring. Still alternatively, $R^{133}$ and $R^{134}$, together with the atom to which they are bonded, can form a 3–12 membered ring. Compounds of Formula XXIX can be produced by converting the diazo compound of Formula XXVIII using a compound having the formula ("Formula XXX"):

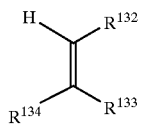

in which $R^{132}$, $R^{133}$, and $R^{134}$ are defined as they are above with regard to Formula XXIX. The reaction is carried out using a dirhodium catalyst composition of the present invention. Other reaction conditions suitable for carrying out this conversion are the same as those discussed above with regard to insertion reactions. The amount of catalyst used in this reaction can be about the same as the amount of catalyst which would be employed if the catalyst were not bound on a solid support. For example, suitable mole ratios of the catalyst to the diazo compound of Formula XXVIII are: from about 1:100,000 to about 1:20, such as from about 1:10,000 to about 1:50, from about 1:1000 to about 1:50, from about 1:500 to about 1:50, and/or from about 1:200 to about 1:100.

Once formed, compounds of Formula XXIX can be used in an number of ways.

For example, compounds of Formula XXIX in which at least one of $R^1$ and $R^2$ is H and in which $R^{132}$ is an electron donating group can be converted to cyclopentenes, for example, by treating the compound of Formula XXIX with a Lewis acid, such as diethyl aluminum chloride. As used herein, "electron donating group" refers to those groups which are able to inject electron density from adjacent positions in a molecule, as determined, for example, by reference to the classification established by the Hammett scale, such as the one set forth in Gordon, which is hereby incorporated by reference. Suitable electron-donating groups include those having a para a value less that or equal to about zero (e.g., less that or equal to about −1, and/or less that or equal to about −2 with reference to the Hammett scale. Particular examples of electron withdrawing groups are alkoxy groups.

Alternatively, compounds of Formula XXIX in which $R^1$ and $R^2$ are H, in which $R^{132}$ is an electron donating group (e.g., an alkoxy group), and in which $R^3$ is a silyloxy group can be converted to dihydrofurans, for example, by treating the compound of Formula XXIX with a fluoride, such as tetrabutylammonium fluoride.

Still alternatively, compounds of Formula XXIX in which at least one of $R^1$ and $R^2$ is H, in which $R^{132}$ is an electron donating group (e.g., an alkoxy group), in which Y is a carboxylic acid ester of the formula —$COOR^{160}$, and in which $R^{160}$ is a tertiary alkyl moiety (e.g., a t-butyl group) can be converted to butenolides, for example, by treating the compound of Formula XXIX with a Lewis acid catalyst, such a boron halide (e.g., $BF_3$ or $BBr_3$) or another Lewis acid catalyst containing boron.

Compounds of Formula XXIX can also be used to prepare compounds having the formula ("Formula XXXI");

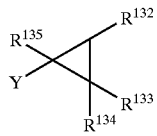

where each of $R^{132}$, $R^{133}$ $R^{134}$, and Y are defined as they were with regard to Formula XXIX and where $R^{135}$ is a carboxylic acid group, a carboxylic acid derivative (e.g., a carboxylic acid ester, a carboxylic acid amide, etc.), or an amino group (e.g., a unsubstituted, monosubstituted, or disubstituted amino group). The conversion of compounds of Formula XXIX to compounds of Formula XXXI in which $R^{135}$ is a carboxylic acid or carboxylic acid derivative can be effected, for example, by treating the compound of Formula XXIX with an oxidative alkene cleavage reagent, such as $RuCl_3/NaIO_4$. Compounds of Formula XXXI in which $R^{135}$ is a carboxylic acid or carboxylic acid derivative can be further converted to compounds of Formula XXXI in which $R^{135}$ is an amino group, for example by treatment with triethylamine, diphenylphosphoryl azide, and t-butyl alcohol; followed by treatment with di-t-butyl dicarbonate to produce a Boc-protected amine; and conversion of the Boc-protected amine to the free amine using, for example, strong acid (e.g., 3 N HCl in EtOAc). Using this method in conjunction with enantiomerically pure compounds of Formula XXIX (formed, for example, by using a dirhodium catalyst composition of the present invention containing a diastereomerically pure dirhodium catalyst), each of the four stereoisomers of 2-phenylcyclopropan-1-amino acid can be produced.

Compounds of Formula XXIX can also be converted to compounds having the formula ("Formula XXXII"):

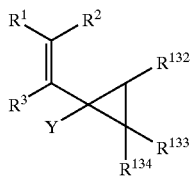

where each of $R^1$, $R^2$, $R^3$, $R^{132}$, $R^{133}$, and $R^{134}$ are defined as they were with regard to Formula XXIX and where Y' is an alkyl group, an aldehyde group, a ketone, or a vinyl group. As one illustrative example, $R^2$ can be H; $R^1$ and $R^3$, together with the atoms to which they are bonded, can form a phenyl group; $R^{132}$ can be H; $R^{133}$ can be a 4-alkoxyphenyl group; $R^{134}$ can be a phenyl group; Y can be a carboxylic acid ester; and Y' can be an aldehyde group, a hydroxymethyl group, a vinyl group, or an ethyl group. Compounds of Formula XXIX can be converted to a compound of Formula XXXII where Y' is a hydroxymethyl group by treating the compound of Formula XXIX with a reducing agent, e.g., LiAlH$_4$, in an inert solvent (e.g., tetrahydrofuran) at an appropriate temperature (e.g. from about –78° C. to about 0° C.). The resulting alcohol can then be oxidized (e.g., under Swern conditions) to produce the compound of Formula XXXII where Y' is an aldehyde group. The aldehyde can then be converted to the corresponding alkene (i.e., a compound of Formula XXXII where Y' is a vinyl group), for example, by treatment with Ph$_3$P=CH$_2$. The alkene can then be hydrogenated (e.g., using Rh/Al$_2$O$_3$) to produce a compound of Formula XXXII where Y' is an ethyl group. For example, using this sequence of reactions in conjunction with a compounds of Formula XXIX in which $R^1$ and $R^3$, taken together with the atoms to which they are bonded, represent a phenyl ring; in which $R^{133}$ is a phenyl group; and in which $R^{134}$ is a 4-(2-chloroethoxy)phenyl group, and further treatment of the resulting compound of Formula XXXII where Y' is an ethyl group with dimethylamine in the presence of sodium iodide in DMF-H$_2$O at appropriate temperature (e.g., about 55° C.), a cyclopropyl analog of tamoxifen can be produced. Using this method in conjunction with enantiomerically pure compounds of Formula XXIX (formed, for example, by using a dirhodium catalyst composition of the present invention containing a diastereomerically pure dirhodium catalyst), the stereochemistry of the chiral centers in this tamoxifen analog can be controlled. Further details regarding the conversion of Compounds of Formula XXIX to compounds of Formula XXXII can be found, for example, in Davies et al., "Stereoselectivity of Methyl Aryldiazoacetate Cyclopropanations of 1,1-Diarylethylene. Asymmetric Synthesis of a Cyclopropyl Analogue of Tamoxifen," *Organic Letters,* 2(6):823–826 (2000), which is hereby incorporated by reference.

Compounds of Formula XXXI can also be used to synthesize compounds having the formula ("Formula XXXIII"):

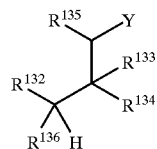

where each $R^{132}$, $R^{133}$, $R^{134}$ and Y are defined as they were with regard to Formula XXXI; where $R^{135}$ is a carboxylic acid group or a carboxylic acid derivative; and where $R^{136}$ represents an aryl group or an alkyl group. The synthesis includes providing a compound having Formula XXXI in which $R^{135}$ is a carboxylic acid group or a carboxylic acid derivative and converting this compound of Formula XXXI to the compound of Formula XXXIII using, for example, an aryl or alkyl cuprate (e.g., having the formula [$R^{136}$—$_2$CuLi$_2$CN).

Compounds of Formula XXXIII in which $R^{135}$ is a carboxylic acid group or a carboxylic acid derivative and in which $R^{132}$ has the formula:

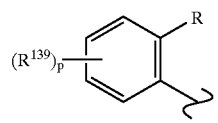

where each $R^{139}$ independently represents an alkyl group, an aryl group, a halogen, a hydroxy group, an amino group, a thiol group, an alkyl thiol group, an aryl thiol group or two or more of $R^{139}$, together with that atoms to which they are bonded, form a 5–12 membered ring; and where p represents an integer from 0 to 4 can be converted to compounds having the formula ("Formula XXXIV"):

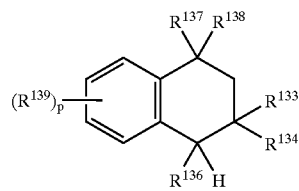

where each of $R^{133}$, $R^{134}$, and $R^{136}$ is defined as it was with regard to Formula XXXIII; where $R^{137}$ is H and $R^{138}$ represents an amino group or $R^{137}$ and $R^{138}$, together with the carbon atom to which they are bonded, represent a carbonyl moiety; and where $R^{139}$ is defined as above. For example, compounds of Formula XXXIII can be decarboxylated and then acylated (e.g., using a Friedel Crafts acylation method) to produce compounds of Formula XXXIV where $R^{137}$ and $R^{138}$, together with the carbon atom to which they are bonded, represent a carbonyl moiety. Reductive amination can be used to convert $R^{137}$ and $R^{138}$ from a =O group to an amine group.

Further details with regard to the aforementioned cyclopropanation reactions and the reactions which use the products of these cyclopropanation reactions can be found, for example, in Davies et al., "Asymmetric Cyclopropanations by Rhodium (II) N-(Arylsulfonyl)prolinate Catalyzed Decomposition of Vinyldiazomethanes in the Presence of Alkenes. Enantioselective Synthesis of the Four Stereoisomers of 2-Phenylcyclopropan-1-amino Acid," *J. Am. Chem.*

Soc., 118(29):6897–6907 (1996); Davies et al., "Stereoselectivity of Methyl Aryldiazoacetate Cyclopropanations of 1,1-Diarylethylene. Asymmetric Synthesis of a Cyclopropyl Analogue of Tamoxifen," *Organic Letters*, 2(6):823–826 (2000); Davies et al., "Effect of Diazoalkane Structure on the Stereoselectivity of Rhodium(II) (S)-N-(Arylsulfonyl) prolinate Catalyzed Cyclopropanations," *Tetrahedron Letters*, 37(24):4133–4136 (1996); Davies et al., "Effect of Catalyst on the Diastereoselectivity of Methyl Phenyldiazoacetate Cyclopropanations," *Tetrahedron Letters*, 39:8811–8812 (1998); Davies et al., "Enantioselective Synthesis of Fused Cycloheptadienes by a Tandem Intramolecular Cyclopropanation/Cope Rearrangement Sequence," *J. Org. Chem.*, 64(23):8501–8508 (1999); Davies, "Rhodium-Stabilized Vinylcarbenoid Intermediates in Organic Synthesis," *Current Organic Chemistry* 2:463–488 (1998); Davies et al., "Effect of Rhodium Carbenoid Structure on Cyclopropanation Chemoselectivity," *Tetrahedron*, 56:4871–4880 (2000); Davies, "Dirhodium Tetra(N-arylsulfonylprolinates) as Chiral Catalysts For Asymmetric Transformations of Vinyl- and Aryldiazoacetates," *Eur. J. Org. Chem.*, pages 2459–2469 (1999); Nagashima et al., "Catalytic Asymmetric Solid-Phase Cyclopropanation," *J. Am. Chem. Soc.*, 123(11):2695–2696 (2001); and Davies, "Asymmetric Synthesis Using Rhodium—Stabilized Vinylcarbenoid Intermediates," *Aldrichimica Acta*, 30(4):107–114 (1997), each of which is hereby incorporated by reference. All of the cyclopropanation reactions set forth in the above-identified references can be modified by using the method and dirhodium catalyst compositions of the present invention. Illustratively, the dirhodium catalyst composition of the present invention can contain about the same amount of dirhodium catalyst as called for in these references.

The above-described reactions exemplify the present invention's usefulness in catalyzing aryldiazomethane or vinyldiazomethane cyclopropanation reactions in which aryldiazomethanes or vinyldiazomethanes are contacted with a dirhodium catalyst composition according to the present invention under conditions effective to catalyze the aryldiazomethane or vinyldiazomethane cyclopropanation reaction. These methods provide new and useful ways to make compounds (such as the compounds illustrated by Formulae XXVII (in cases where $R^{130}$, $R^{130}$, and the carbon to which they are bonded form a cyclopropane moiety), XXIX, and XXXI–XXXIV) and to produce C—C bonds.

The method and composition of the present invention can also be used to produce optionally substituted cycloheptadienes or optionally substituted bicyclooctadienes. In this method, a diazo compound having the formula ("Formula XXXV"):

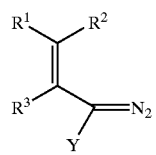

is provided. In Formula XXXV, Y is an electron withdrawing group; and $R^1$, $R^2$, and $R^3$ are independently selected from H, alkyl, aryl, silyloxy, or vinyl, or $R^1$ and $R^3$, together with the atoms to which they are bonded, form a 5–12 membered ring. The diazo compound having the Formula XXXV is then converted with a optionally substituted homocyclic, heterocyclic, or non-cyclic diene. Suitable optionally substituted homocyclic, heterocyclic, or non-cyclic diene include those having the formula ("Formula XXXVI"):

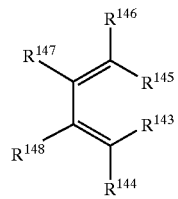

In Formula XXXVI, each of $R^{144}$, $R^{146}$, $R^{147}$, and $R^{148}$ independently represent an alkyl group, an aryl group, an alkoxy group, a halogen, hydrogen, an acyl group, a hydroxy group, a thiol group, an alkyl thiol or aryl thiol group, a carboxylic acid group, a carboxylic acid derivative, or a silyloxy group, or two or more of $R^{144}$, $R^{146}$, $R^{147}$, and $R^{148}$, together with the atom or atoms to which they are bonded, form a 5–12 membered ring. Each of $R^{143}$ and $R^{145}$ independently represents an alkyl group, an aryl group, an alkoxy group, a halogen, hydrogen, an acyl group, a hydroxy group, a thiol group, an alkyl thiol or aryl thiol group, a carboxylic acid group, a carboxylic acid derivative, or a silyloxy group, or $R^{143}$ and $R^{145}$ together represent a —O— moiety, a —S— moiety, a substituted or unsubstituted bivalent amino moiety (e.g., a substituted or unsubstituted bivalent amino moiety having the formula —N($R^{150}$)— in which $R^{150}$ is H, an aryl group, or alkyl group), or a substituted or unsubstituted methylene or ethylene moiety. Examples of optionally substituted cycloheptadienes or optionally substituted bicyclooctadienes that can be produced using this method include optionally substituted cyclohepta-1,5 dienes and optionally substituted 8-azabicyclo [3.2.1]octa-2,6 dienes, such as those having the formula ("Formula XXXVII"):

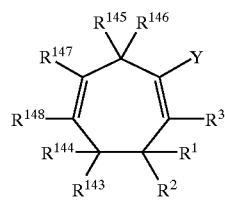

in which $R^{143}$, $R^{144}$, $R^{145}$, $R^{146}$, $R^{147}$, and $R^{148}$ have the same meanings as set forth above with regard to Formula XXXVI and in which $R^1$, $R^2$, $R^3$, and Y have the same meanings as set forth above with regard to Formula XXXV. The reaction is carried out using a dirhodium catalyst composition of the present invention. Other reaction conditions suitable for carrying out the conversion of compounds having Formula XXXV with optionally substituted homocyclic, heterocyclic, or non-cyclic diene are the same as those discussed above with regard to insertion reactions. The amount of catalyst used in this reaction can be about the same as the amount of catalyst which would be employed if the catalyst were not bound on a solid support. For example, suitable mole ratios of the catalyst to the diazo compound of Formula XXXV are: from about 1:100,000 to about 1:20, such as from about 1:10,000 to about 1:50, from about 1:1000 to about 1:50, from about 1:500 to about 1:50, and/or from about 1:200 to about 1:100. These reactions can be carried out stereospecifically, for example with enantiomerically pure dirhodium catalysts (such as enantiomerically pure dirhodium catalysts having $D_2$ symmetry), such as those depicted in Formulae IV and VII–XII. Alternatively, the reaction can be carried out racemically, in which case any dirhodium tetracarboxylate catalyst can be employed.

Compounds of Formula XXXVII in which $R^{143}$ and $R^{145}$ together represent a substituted or unsubstituted bivalent amino moiety having the formula —N($R^{150}$)— (in which $R^{150}$ is H, an aryl group, or alkyl group) can be readily converted to 3-aryltropanes, for example by reaction the compound of Formula XXXVII with a Grignard reagent (e.g., having the formula $R^{151}$—Mg—X, where $R^{151}$ is an aryl group and X is a halogen). Illustratively, the 3-aryltropane can have the formula ("Formula XXXVIII"):

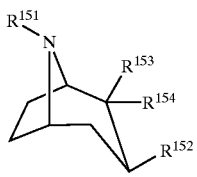

where $R^{151}$ is H, an aryl group, or an alkyl group; $R^{152}$ is an aryl group; $R^{153}$ represents H or a C1–C12 ketone; and $R^{154}$ represents H or a C1–C12 ketone. Further details regarding the dirhodium catalyzed preparation of cycloheptadienes and bicyclooctadienes, as well as the production of tropanes and other useful materials from these cycloheptadienes and bicyclooctadienes are available in U.S. Pat. No. 5,760,055 to Davies; U.S. Pat. No. 5,591,854 to Davies; Davies, "[3+4] Annulations Between Rhodium—Stabilized Vinylcarbenoids and Dienes," *Advances in Cycloaddition*, 5:119–164 (1999); Davies et al., "Tandem Asymmetric Cyclopropanation/Cope Rearrangement. A Highly Diastereoselective and Enantioselective Method for the Construction of 1,4-Cycloheptadienes," *J. Am. Chem. Soc.*, 120(4): 3326–3331 (1998); Davies et al., "Enantioselective Synthesis of Functionalized Tropanes by Rhodium(II) Carboxylate-Catalyzed Decomposition of Vinyldiazomethanes in the Presence of Pyrroles," *J. Org. Chem.*, 62(4):1095–1105 (1997); Davies et al., "Effect of Rhodium Carbenoid Structure on Cyclopropanation Chemoselectivity," *Tetrahedron*, 56:4871–4880 (2000); Davies et al., "Enantioselective Synthesis of Fused Cycloheptadienes by a Tandem Intramolecular Cyclopropanation/Cope Rearrangement Sequence," *J. Org. Chem.*, 64(23):8501–8508 (1999); Davies, "Rhodium—Stabilized Vinylcarbenoid Intermediates in Organic Synthesis," *Current Organic Chemistry*, 2:463–488 (1998); and Davies, "Asymmetric Synthesis Using Rhodium—Stabilized Vinylcarbenoid Intermediates," *Aldrichimica Acta*, 30(4):107–114 (1997), each of which is hereby incorporated by reference.

The above-described reactions exemplify the present invention's usefulness in catalyzing [3+4] annulation reactions in which vinyldiazomethanes are reacted, for example, intermolecularly with a diene by contacting the vinyldiazomethane with a dirhodium catalyst composition of the present invention under conditions effective to produce a seven or eight membered ring or ring system. It should be noted that these reactions can also be carried out intramolecularly with a diene moiety contained in the vinyldiazomethane. These methods provide new and useful ways to make compounds (such as the compounds illustrated by Formulae XXXVII and XXXVIII) and to produce seven or eight membered rings and/or seven or eight membered ring systems (e.g., bicyclooctadiene ring systems).

The method and composition of the present invention can also be used to produce a compound having the formula ("Formula XXXIX"):

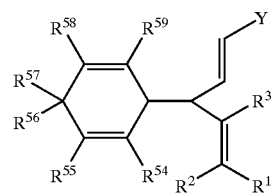

In Formula XXXIX, $R^1$, $R^2$, and $R^3$ are independently selected from H, alkyl, aryl, or vinyl, or $R^1$ and $R^3$, together with the atoms to which they are bonded, form a 5–12 membered ring, such as a cyclohexene ring, or a cyclohexa-1,3-diene ring. Illustratively, the method can be used to prepare compounds in which $R^1$ and $R^3$, together with the atoms to which they are bonded, form an aromatic ring, such as a 3,4-dichlorophenyl ring, in which case the compound produced can have the formula ("Formula XL"):

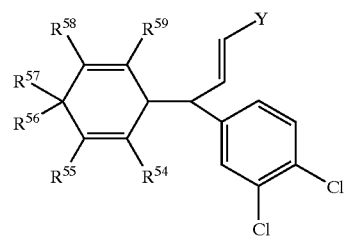

in which Y is an electron withdrawing group, examples of which include moieties having the formulae: —C(O)$R^{77}$, —SO$_2$$R^{77}$, and —P(O)$R^{77}R^{77'}$. In these formulae, each of $R^{77}$ and $R^{77'}$ is independently selected from an alkyl group, an aryl group, and an alkoxy group. For example, Y can have the formula CO$_2$$R^{12}$ where $R^{12}$ is an alkyl group or an aryl group.

Each of $R^{54}$, $R^{55}$, $R^{56}$, $R^{57}$, $R^{58}$, and $R^{59}$ is independently selected from the group consisting of H, alkyl, aryl, halogen, and alkoxy.

The method includes providing a 1,3-cyclohexadiene having the formula ("Formula XLI"):

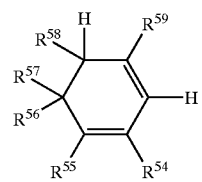

where $R^{54}$, $R^{55}$, $R^{56}$, $R^{57}$, $R^{58}$, and $R^{59}$ are defined as above with regard to Formula XL. The method further includes converting the 1,3-cyclohexadiene with a diazo compound having the formula ("Formula XLII"):

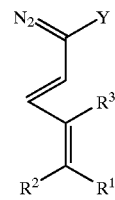

in which Y, $R^1$, $R^2$, and $R^3$ are as defined above in the presence of a rhodium catalyst composition of the present invention.

Illustratively, the reaction can be carried out by contacting the catalyst composition with the 1,3-cyclohexadiene of Formula XLI. Alternatively, the catalyst composition can be first contacted with the diazo compound of Formula XLII. Still alternatively, the 1,3-cyclohexadiene of Formula XLI can first be combined with the diazo compound of Formula XLII, and then the catalyst composition can be contacted with this combination. In the case where the 1,3-cyclohexadiene of Formula XLI is a liquid (e.g., in the case where the compound of Formula XLI is 1,3-cyclohexadiene), the reaction can be carried out without the use of additional solvent. Alternatively, the mixture can be formed using an inert solvent or a solvent which is significantly less reactive towards the diazo compound of Formula XLII than is the compound of Formula XLI. Suitable solvents include alkanes, such as hexanes. The solvent can be dried prior to use using conventional methods; and the reaction vessel can also be dried, such as by flaming or in an oven. The amount of catalyst used in this reaction can be about the same as the amount of catalyst which would be employed if the catalyst were not bound on a solid support. For example, suitable mole ratios of the catalyst to the diazo compound of Formula XLII are: from about 1:100,000 to about 1:20, such as from about 1:10,000 to about 1:50, from about 1:1000 to about 1:50, from about 1:500 to about 1:50, and/or from about 1:200 to about 1:100.

Once the catalyst composition is contacted with the compound of Formula XLI, the compound of Formula XLII is added, for example with stirring. Addition can be carried out in a single portion, continuously, or batchwise. Slow, dropwise can be effected, for example, by using a syringe pump. The amount of compound of Formula XLII added is generally dependent on the amount of compound of Formula XLI present in the reaction mixture. For example, the mole ratio of compound of Formula XLII to compound of Formula XLI can be from about 1:10 to about 10:1, such as from about 1:8 to about 1:1 and/or from about 1:6 to about 1:4. The addition can be carried out at any suitable temperature from the freezing point to the boiling point of the solvent and/or the compound of Formula XLI. Illustratively, the addition can be carried out from about −50° C. to about 60° C., such as at about room temperature. In certain embodiments, higher temperatures may favor a reverse Cope rearrangement, in which case, compounds having Formula XXXIX rearrange to form compounds having the formula ("Formula XLIII"):

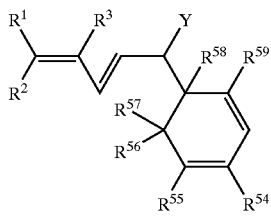

The method is suitable for making compounds having Formula XL which are substantially enantiomerically pure, such as, for example, compounds having the formula ("Formula XLIV"):

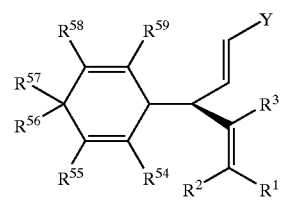

such as compounds having the formula ("Formula XLV"):

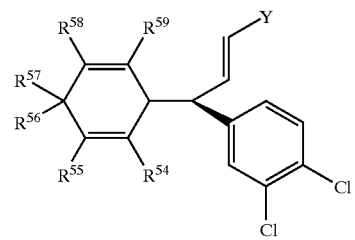

In one embodiment of the present invention, a substantially enantiomerically selective reaction is desired, and a chiral catalyst, such as one having $D_2$ symmetry, is employed. For example, by using one of the catalysts depicted in Formulae IV and VII–XII, compounds of Formulae XLIV and XLV which are substantially enantiomerically pure (e.g., >80% ee, >90% ee, >95% ee, >98% ee, and/or >99% ee) can be prepared.

The cyclohexadiene derivative of Formula XXXIX wherein $R^{57}$ is H can be converted into a compound having the formula ("Formula XLVI"):

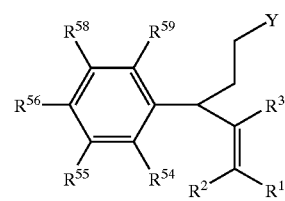

in which $R^1$, $R^2$, $R^3$, $R^{54}$, $R^{55}$, $R^{56}$, $R^{58}$, $R^{59}$, and Y are defined as they were above for the compounds having Formula XXXIX. The conversion can be carried out with hydrogenating and oxidizing agents under conditions effective to form the compound of Formula XLVI. The hydrogenation and oxidation reactions can be carried out simultaneously or sequentially, and, when carried out sequentially, hydrogenation can precede oxidation or oxidation can precede hydrogenation. Suitable hydrogenating agents for use in the present reaction include hydrogen gas in combination with a metal catalyst, such as palladium (e.g., palladium on carbon). Suitable conditions for carrying out such reactions are described in House, *Modern Synthetic Reactions*, 2nd ed., Menlo Park, Calif.: The Benjamin/ Cummings Publishing Company, pp. 1–34 (1972) ("House"), which is hereby incorporated by reference. Suitable oxidizing agents for use in the present reaction include those which are generally known to dehydrogenate 1,4-cyclohexadienyl moieties to phenyl moieties, such as 2,3-dichloro-5,6-dicyano-1,4-benzoquinone ("DDQ") and tetrachlorobenzoquinone (a.k.a., chloranil). Other suitable oxidizing agents and suitable conditions for carrying out such reactions are described, for example, at pages 33–44 of House, which is hereby incorporated by reference.

The above-described method is useful for making compounds having Formula XLVI in which Y is an alkoxycarbonyl group (e.g., in which Y has the formula —COOR$^{12}$ and R$^{12}$ is an alkyl group) and/or in which R$^1$ and R$^3$, together with the atoms to which they are bonded, form an aromatic ring, such as a 3,4-dichlorophenyl ring. In the latter case, the compound of Formula XLVI has the formula ("Formula XLVII"):

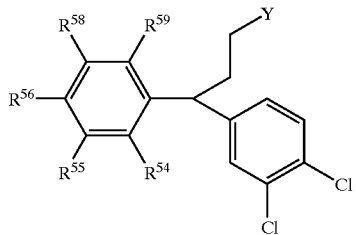

Furthermore, by using a cyclohexadiene having Formula XLIV (e.g., a cyclohexadiene having Formula XLV), substantially enantiomerically pure compounds of Formula XLVI, such as those having the formula ("Formula XLVIII"):

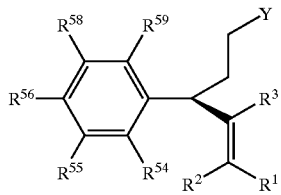

for example, those having the formula ("Formula XLIX"):

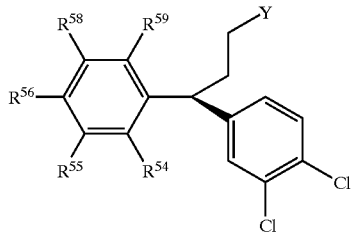

can be prepared.

The compound having Formula XLVI can be used to make a compound having the formula ("Formula L"):

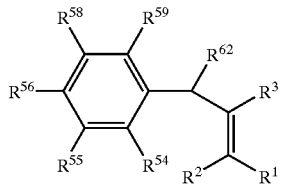

where R$^1$, R$^2$, R$^3$, R$^{54}$, R$^{56}$, and R$^{58}$ are defined as they were with regard to Formula XLVI. R$^{62}$ represents an alkyl moiety, examples of which include methyl, ethyl, or propyl groups, which can optionally be substituted with, for example, aryl groups (optionally containing a heteroatom) (e.g., pyrid-4-ylmethyl) or amino groups (which are meant to include amines that are unsubstituted or mono- or di-substituted with, for example, alkyl or aryl groups) (e.g., 2-(N,N-diisopropylamino)ethyl). Alternatively, R$^{65}$ and R$^{62}$ together represent the atoms necessary to complete a 5–12 membered ring, in which case the compound produced has the formula ("Formula LI"):

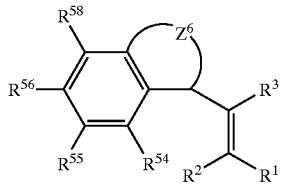

In this formula, Z$^6$ represents, for example, an alkylene group (e.g., a group having the formula —CH$_2$CH$_2$—, —CH$_2$CH$_2$CH$_2$—, —CH(NH$_2$)CH$_2$CH$_2$—, —CH$_2$CH$_2$CH(NH$_2$)—, —CH$_2$NRCH$_2$—, —CH$_2$CH(C$_6$H$_5$)CH$_2$—, etc.). Specific compounds of Formula L which can be made using this method include 1,1-diarylalkanes, such as the pharmaceuticals tolterodine and CDP-840, which respectively have the formulae:

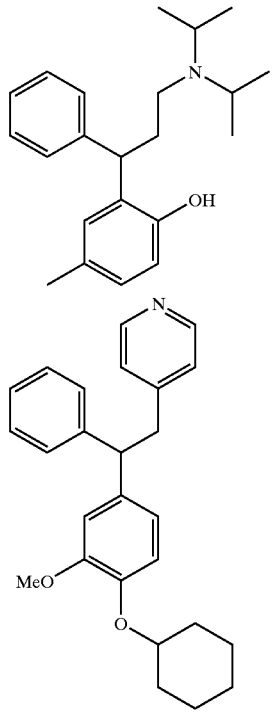

as well as nominfensine and sertraline, which respectively have the formulae:

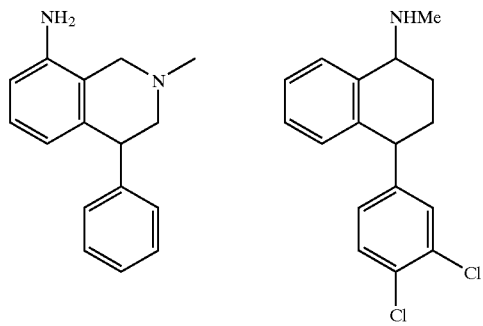

Conditions effective for achieving the conversion of compounds of Formula XLVI to compounds of Formula L depend on the nature of the desired substituents at $R^{62}$ and $R^{65}$. Illustratively, in the case where $R^{62}$ and $R^{65}$ are discreet moieties (i.e., in the case where $R^{62}$ and $R^{65}$ do not combine to form a ring structure), $R^{59}$ can be chosen so that no further chemistry is required at that position to obtain the desired $R^{65}$ substituent, and the —CH$_2$CH$_2$Y moiety can be converted to the desired $R^{62}$ substituent using conventional methods. In the case where $R^{62}$ and $R^{65}$ combine to form a ring, conventional cyclization chemistry can be employed. For example, in the case where $R^{59}$ is H and $R^{62}$ and $R^{65}$ together represent a —CH$_2$CH$_2$CH$_2$— moiety, cyclization can be carried out using, for example, a Friedel—Crafts acylation catalyst.

The above method for making compounds having Formula LI is illustrated by the following procedure for making sertraline or sertraline congeners having the formula ("Formula LII"):

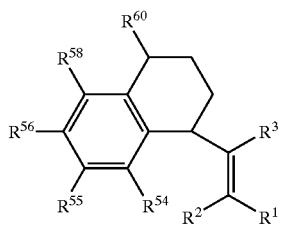

In Formula LII, $R^1$, $R^2$, $R^3$, $R^{54}$, $R^{55}$, $R^{56}$ and $R^{58}$ defined as they were above with regard to compounds of Formula XLVI. $R^{60}$ is H. $R^{61}$ can represent a substituted or unsubstituted amine, such as an amine having the formula —NR$^{63}$R$^{64}$, where each of $R^{63}$ and $R^{64}$ is independently selected from hydrogen, an alkyl group, and an aryl group. Illustratively, $R^{61}$ can be a dialkyl amino group (e.g., N(CH$_3$)$_2$), a monoalkylamino group (e.g., —NHCH$_2$CH$_3$), or a monoarylamino group (e.g., —NH(C$_6$H$_5$)), or $R^{61}$ can represent a cyclic amine moiety, such as a piperidinyl group or a morpholino group. Alternately, $R^{60}$ and $R^{61}$, together with the carbon atom to which they are bonded, can represent a carbonyl (i.e., a C=O) moiety.

The method includes providing a cyclohexadiene derivative having Formula XXXIX in which Y is an electron withdrawing group, such as any one of the electron-withdrawing groups described above, and $R^{57}$ and $R^{59}$ are H. Cyclohexadiene derivatives which can be used in this reaction are those described above. Once the cyclohexadiene derivative is provided, it is converted with hydrogenating, oxidizing, and cyclizing agents under conditions effective to form the compound of Formula LII. The hydrogenation and oxidation reactions can be carried out simultaneously or sequentially, and, when carried out sequentially, hydrogenation can precede oxidation or oxidation can precede hydrogenation. Illustratively, both hydrogenation and oxidation can precede cyclization, as in the case where the cyclohexadiene derivative is converted with a hydrogenating agent and an oxidizing agent into a compound of Formula XLVI and where the phenyl derivative is then converted with a cyclizing agent under conditions effective to produce the compound.

Suitable hydrogenating and oxidizing agents and methods for their use are described above. Cyclizing agents suitable for use in the practice of the present invention include acylation catalysts, such as Friedel Crafts acylation catalysts, examples of which include ClSO$_3$H, AlCl$_3$, and other Lewis acids. In the case where Y is an alkoxycarbonyl group, the alkoxy group can be converted to a hydroxy group, prior to treatment with the Friedel Crafts acylation catalyst. This can be done using strong acid, e.g., 6 N HCl, or by any other suitable method. The immediate product of such a cyclization is a tetralone having the formula ("Formula LIII"):

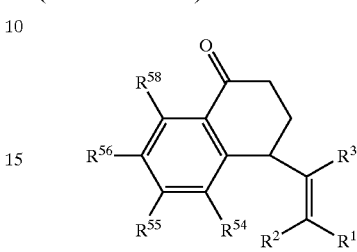

which can be readily converted to compounds having Formula LII by methods known to those skilled in the art, such as the reductive amination method set forth in Corey et al., *Tetrahedron Lett.*, 35:5373–5376 (1994), which is hereby incorporated by reference.

The above-described method is useful for making compounds having Formula LII in which Y is an alkoxycarbonyl group (e.g., in which Y has the formula —COOR$^{12}$ and $R^{12}$ is an alkyl group) and/or in which $R^1$ and $R^3$, together with the atoms to which they are bonded, form an aromatic ring, such as a 3,4-dichlorophenyl ring, in which case the compound of Formula LII can have the formula ("Formula LIV"):

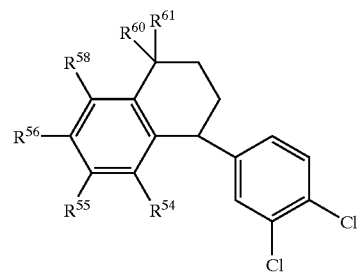

Furthermore, by using a cyclohexadiene having Formula XL (e.g., a cyclohexadiene having Formula XLV), substantially enantiomerically pure compounds of Formula LII, such as those having the formula ("Formula LV"):

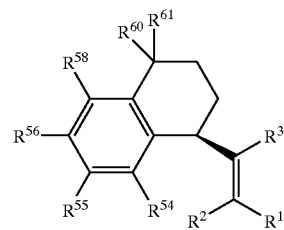

for example, those having the formula ("Formula LVI"):

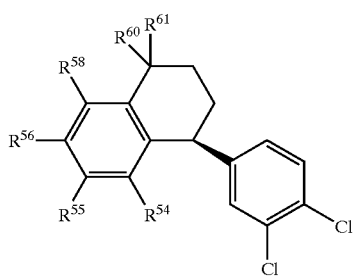

can be prepared.

Further details regarding these reactions as well as further discussion regarding the synthesis of diarylacetates, 4,4-diarylbutanoates, and other ω,ω-diarylalkanoates are set forth, for example, in Davies et al., "Catalytic Asymmetric Synthesis of Diarylacetates and 4,4-Diarylbutanoates. A Formal Asymmetric Synthesis of (+)-Sertraline," *Organic Letters*, 1(2):233–236 (1999), which is hereby incorporated by reference.

Other reactions that can benefit by the practice of the methods and use of the compositions of the present invention include those described in Davies et al., "Effect of Carbenoid Structure on the Reactions of Rhodium—Stabilized Carbenoids with Cycloheptatriene," *Tetrahedron Letters*, 41:2035–2038 (2000) and U.S. Pat. No. 5,175,311 to Doyle, which are hereby incorporated by reference.

Further details with regard to methods for using the compositions of the present invention are set forth below in the section labeled "Examples".

Once the catalytic reaction is completed (or, if desired, even before completion of the reaction), the rhodium catalyst composition of the present invention can be separated from the reaction mixture, for example, for reuse in a subsequent reaction. The exact method for effecting such separation depends, in part, on the nature of the solid support used in the rhodium catalyst composition. For example, where the solid support used in the rhodium catalyst composition is in the form of beads (or where the solid support is coated onto an inert bead substrate, e.g., glass or stainless steel beads), separation can conveniently be achieved by filtration, centrifugation, etc.). Other methods for separating catalysts from reaction mixtures include those well known in the art of heterogeneous catalysis.

The present invention is further illustrated by the following non-limiting examples.

EXAMPLES

Example 1

Preparation and Catalytic Properties of Dirhodium Catalyst Compositions

In order to immobilize chiral dirhodium tetracarboxylate catalysts 1–3 without resorting to ligand modification, we decided to study the use of polymer-supported pyridines.

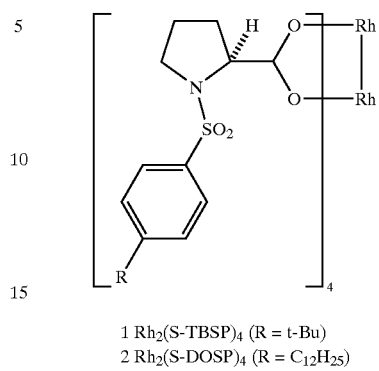

1 $Rh_2(S\text{-}TBSP)_4$ (R = t-Bu)
2 $Rh_2(S\text{-}DOSP)_4$ (R = $C_{12}H_{25}$)

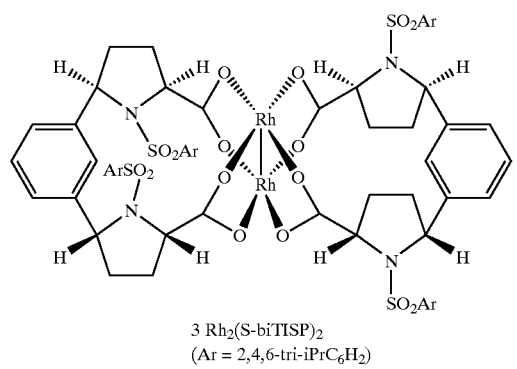

3 $Rh_2(S\text{-}biTISP)_2$
(Ar = 2,4,6-tri-iPr$C_6H_2$)

In this regard, we hypothesized that such polymer-supported pyridines may interact with the dirhodium tetracarboxylate catalysts as shown in Scheme 1. More particularly, we hypothesized that the dirhodium complex could coordinate to the polymer-supported pyridine to form 4, and the other rhodium center in 4 could react with diazo compounds to form the corresponding carbenoid 5.

SCHEME 1

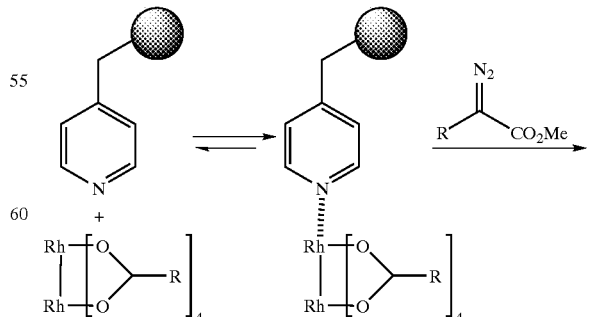

4

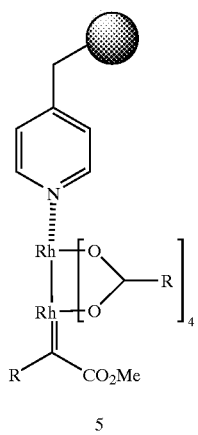

ArgoPore® resin, modified with a pyridinyl group attached to the polymer backbone via a benzyl spacer, was used as the solid support. Referring to Scheme 2, the hydroxy group in ArgoPore®-Wang resin (hydroxyl loading=0.65 mmol/g) (available from Argonaut Technologies) was converted to the bromide 6 with $PPh_3$ and $CBr_4$, and 6 was reacted with the sodium alkoxide of 4-pyridinylmethanol to give 7. To immobilize $Rh_2(S\text{-}TBSP)_4$, the pyridine resin 7 was gently stirred with $Rh_2(S\text{-}TBSP)$ 4 in dichloromethane. The color of the resin changed from pale brown to purple indicating coordination of the pyridine to the rhodium metal. After filtration of the solvent, the resin was washed with dichloromethane (9 times), and was dried under vacuum. In a similar way, $Rh_2(S\text{-}biTISP)_2$ was immobilized on the resin 7. The loading of the rhodium complex was estimated by the increase of the weight of the resin. The loading of $Rh_2(S\text{-}TBSP)_4$ in 7 was 0.18 mmol/g, and that of $Rh_2$ $(S\text{-}biTISP)_2$ was 0.17 mmol/g.

SCHEME 2

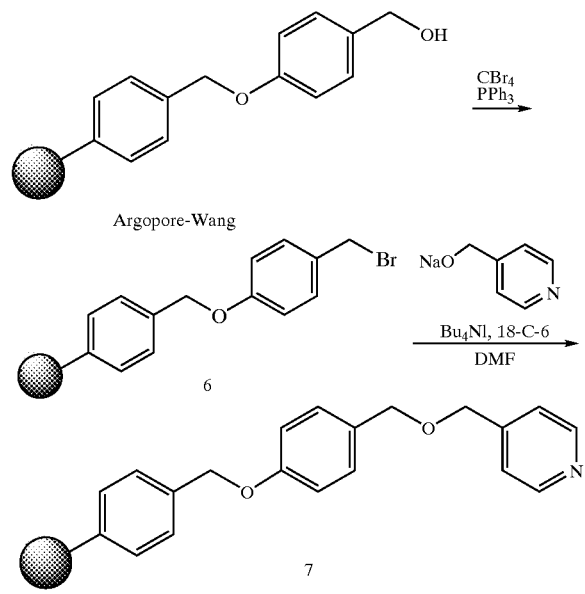

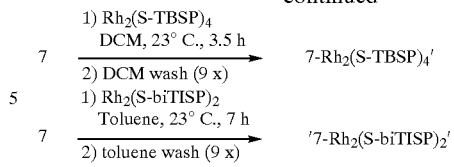

A standard cyclopropanation was used to evaluate the catalytic activity of '7-$Rh_2(S\text{-}TBSP)_4$' and '7-$Rh_2(S\text{-}biTISP)_2$'. Dropwise addition of methyl phenyldiazoacetate to a solution of styrene (2 equiv) with the resin (0.5 mol %) in toluene as solvent resulted in efficient cyclopropanation. The rate of the reaction was found to depend on the rate of stirring, and so all the reactions were run with approximately the same stirring rate. The end-point of the reaction was judged by the cessation of the evolution of nitrogen gas. The resin was rinsed with toluene (5 times) and dried before re-use in the next cycle.

As shown in Table 1, the cyclopropanation with '7-$Rh_2(S\text{-}TBSP)_4$' gave the cyclopropanation product in good yield (92–89%) and diastereoselectivity (>94% de); however, the enantiomeric excess (ee) dropped steadily from 82% to 70% over 4 cycles.

TABLE 1

| 7-Rh$_2$(S-TBSP)$_4$ | | | 7-Rh$_2$(S-biTISP)$_2$ | | |
|---|---|---|---|---|---|
| Cycle | time (min) | yield (%) | ee (%) | Cycle | time (min) | yield (%) | ee (%) |
| 1 | 10 | 92 | 82 | 1 | 18 | 91 | 85 |
| 2 | 17 | 91 | 78 | 2 | 23 | 91 | 86 |
| 3 | 14 | 89 | 73 | 3 | 26 | 90 | 87 |
| 4 | 14 | 89 | 70 | 4 | 36 | 90 | 87 |
|  |  |  |  | 10 | 60 | 87 | 88 |
|  |  |  |  | 15 | 92 | 89 | 88 |

We believe that this indicates that the prolinate catalysts are undergoing slow degradation under the reaction conditions. This would also explain why there is a drop in enantioselectivity using recycled catalyst. In contrast, '7-$Rh_2(S\text{-}biTISP)_2$' appears to be a very robust catalyst as the yield (87–91%) and the enantioselectivity (85–88% ee) remain steady over 15 cycles. The only change is in the reaction time, which increases by a factor of six over the 15 cycles. '7-$Rh_2(S\text{-}TBSP)_4$' gave the (S,S)-cyclopropane, and '7-$Rh_2(S\text{-}biTISP)_2$' gave the (R,R)-cyclopropane. In order to further evaluate the catalytic activity of '7-$Rh_2(S\text{-}biTISP)_2$', the reactions of several diazo compounds using lower equivalents of the catalyst were examined. As shown in Table 2, the reaction with methyl phenyldiazoacetate (entry 1) was similarly achieved (88% yield, 88% ee) with 0.04 mol % of '7-$Rh_2(S\text{-}biTISP)_2$', but the reaction took 3 h to reach completion. With the other aryldiazoacetates (entries 2–5), 0.1 mol % of the catalyst was used and high yields and enantioselectivities of the products were consistently obtained (entries 2–5). The styryldiazoacetate (entry 6) was also effective, but the reaction was slower than that of the aryldiazoacetates.

TABLE 2

Ph-CH=CH$_2$ (1 mmol) + R-C(N$_2$)-CO$_2$Me (0.5 mmol) →[7-Rh$_2$(S-biTISP)$_2$, toluene, 23° C.] cyclopropane product (R, Ph, CO$_2$Me)

| entry | R | time (min) | catalyst (mol %) | yield (%) | ee (%) |
|---|---|---|---|---|---|
| 1 | phenyl | 180 | 0.04 | 88 | 88 |
| 2 | 2-naphthyl | 120 | 0.1 | 89 | 74 |
| 3 | 4-MeO-phenyl | 60 | 0.1 | 90 | 80 |
| 4 | 4-Me-phenyl | 60 | 0.1 | 89 | 83 |
| 5 | 4-Br-phenyl | 60 | 0.1 | 87 | 90 |
| 6 | styryl (PhCH=CH–) | 420 | 0.1 | 82 | 68 |

To investigate the whether the immobilized dirhodium catalyst compositions can be used to prepare compound libraries, a series of cyclopropanations was carried out using recycled catalyst. The results are summarized in Table 3. The yields and the ee's are comparable to those obtained with the 'fresh' catalyst, the latter being shown in Table 2. With 0.5 mol % of the catalyst, all the reactions were completed within 30 min. Furthermore, from the $^1$H NMR spectra of the crude mixture, there was no cross-contamination between successive cyclopropanations. This would indicate that the product is efficiently washed from the polymer support between cycles even though the catalyst is retained.

TABLE 3

Ph-CH=CH$_2$ (1 mmol) + R-C(N$_2$)-CO$_2$Me (0.5 mmol) →[●—Rh$_2$(S-biTISP)$_2$, toluene, 23° C.] cyclopropane product (Ph, R, CO$_2$Me)

| cycle | R | reaction time (min) | yield (%) | ee (%) |
|---|---|---|---|---|
| 1 | styryl (PhCH=CH–) | 16 | 82 | 71 |
| 2 | 2-naphthyl | 30 | 86 | 76 |
| 3 | 4-MeO-phenyl | 5 | 84 | 80 |
| 4 | 4-Me-phenyl | 30 | 85 | 80 |
| 5 | 4-Br-phenyl | 30 | 94 | 90 |

In some regards, the success of this chemistry is surprising because donor groups such as pyridine tend to deactivate dirhodium tetracarboxylates. Therefore, control experiments were carried out to further understand the unexpectedly high efficiency of the '7-Rh$_2$(S-biTISP)$_2$' catalyst composition.

To study the effect of pyridine, both Rh$_2$(S-TBSP)$_4$ and Rh$_2$(S-biTISP)$_2$ were mixed with 1.5 equiv of 4-alkylpyridine 8, as shown in Scheme 3.

SCHEME 3

Ph-CH=CH$_2$ + Ph-C(N$_2$)-CO$_2$Me → cyclopropane (Ph, Ph, CO$_2$Me)

| catalyst | time, min | yield, % | ee, % |
|---|---|---|---|
| Rh$_2$(S-TBSP)$_4$/8 | 10 | 43 | 81 |
| Rh$_2$(S-biTISP)$_2$/8 | 720 | 18 | 88 |

SCHEME 3

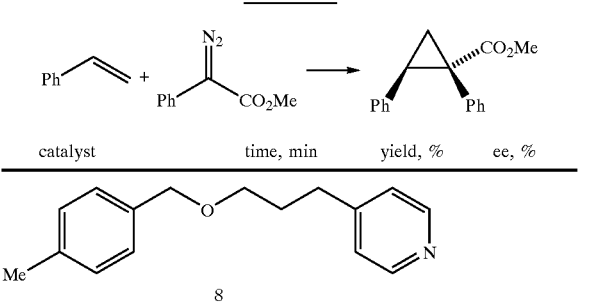

| catalyst | time, min | yield, % | ee, % |
|---|---|---|---|

The cyclopropanation of styrene with phenyldiazoacetate using these catalysts was conducted in toluene. With $Rh_2$(S-TBSP)$_4$ coordinated to 8, the reaction was complete in 10 min but the yield was only 43%. $Rh_2$(S-biTISP)$_2$ coordinated to 8 showed very little catalytic activity. Even after 12 h, the yield of cyclopropanation was only 18%, and many unidentified side products were observed by $^1$H NMR of the crude mixture. In both cases, however, enantioselectivity remained high. These results suggest that coordination of pyridine to $Rh_2$(S-biTISP)$_2$ significantly decreases its catalytic activity and that, in the '7-$Rh_2$(S-biTISP)$_2$' catalyst, the 'active' catalyst is not $Rh_2$(S-biTISP)$_2$ coordinated to the pyridine.

In order to further determine the importance of the pyridine group, a second control experiment was undertaken, as shown in Scheme 4. The analogous phenyl-substituted resin 9 was prepared, and it was found that it also could immobilize $Rh_2$(S-TBSP)$_4$ and $Rh_2$(S-biTISP)$_2$. The resin 9 was treated with either $Rh_2$(S-TBSP)$_4$ or $Rh_2$(S-biTISP)$_2$ in toluene, and the resin was then washed with toluene (5 times). The resulting green-colored resins contained 0.11 mmol/g of $Rh_2$(S-TBSP)$_4$, and 0.07 mmol/g of $Rh_2$(S-biTISP)$_2$, respectively.

SCHEME 4

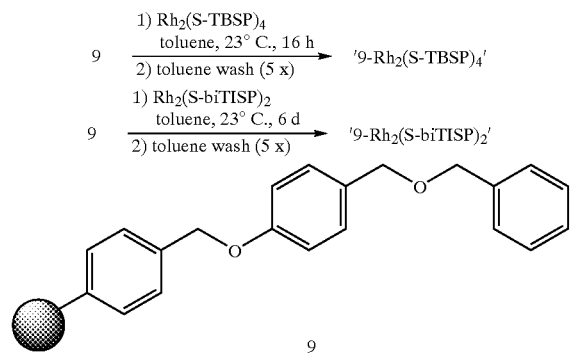

With the phenyl-substituted resin catalysts, five cycles of cyclopropanation of styrene with methyl phenyldiazoacetate were tried. As shown in Table 4, the reaction with the phenyl resin '9-$Rh_2$(S-TBSP)$_4$' gave the cyclopropanation product in good yields (90–92%); however, the enantioselectivity dropped slightly from 85% to 81% ee. The reaction with the phenyl-resin '9-$Rh_2$ (S-biTISP)$_2$' maintained the same level of enantioselectivity over four cycles; however, longer reaction times were required to complete the reaction.

TABLE 4

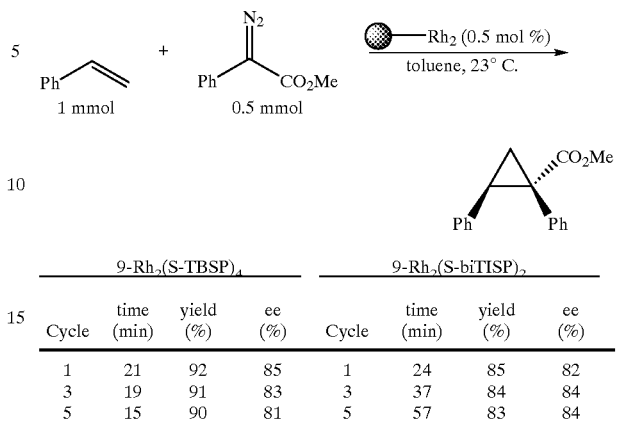

| | 9-$Rh_2$(S-TBSP)$_4$ | | | | 9-$Rh_2$(S-biTISP)$_2$ | | |
|---|---|---|---|---|---|---|---|
| Cycle | time (min) | yield (%) | ee (%) | Cycle | time (min) | yield (%) | ee (%) |
| 1 | 21 | 92 | 85 | 1 | 24 | 85 | 82 |
| 3 | 19 | 91 | 83 | 3 | 37 | 84 | 84 |
| 5 | 15 | 90 | 81 | 5 | 57 | 83 | 84 |

These control experiments suggest that, perhaps, the actual catalyst in the pyridine-resin 7 is not the pyridine coordinated dirhodium complex. At present, it is not clear whether catalyst immobilization in the nitrogen-containing solid support/catalyst compositions is due to a microencapsulation effect (as is likely to be the case where the phenyl-containing solid support/catalyst is employed) or whether catalyst immobilization in the nitrogen-containing solid support/catalyst compositions is due to a coordination of the nitrogen atom to a rhodium atom. Irrespective of the mechanism of binding, the results demonstrate that dirhodium catalysts can be immobilized or otherwise bound to solid supports, that the catalyst/solid support compositions are active as catalysts, and that the catalyst/solid support compositions can be recycled 15 times, while the products are readily removed by solvent washing.

Example 2

Preparation of 4-(Bromomethyl)phenoxymethyl-polystyrene (6)

To a suspension of Argopore-Wang Resin (loading 0.65 mmol/g, 1.04 g, 0.676 mmol) in dichloromethane ("DCM") (7 mL) was added $CBr_4$ (0.607 g, 1.83 mmol). After cooling to 0° C. (ice-water bath), $PPh_3$ (0.385 g, 1.46 mmol) in DCM (1 mL) was added. After 2.5 h, the cooling bath was removed, and the mixture was stirred for 3 h at 23° C. The solvent was removed by filtration. The resin was washed with DCM (8×25 mL), and the recovered solid was air dried under vacuum to give 0.95 g of resin.

Example 3

Preparation of 4-[4-(Pyridinyl)methoxymethyl] phenoxymethyl-polystyrene (7)

To NaH (60% in mineral oil, 66 mg, 1.64 mmol) was added a solution of 4-pyridinecarbinol (0.250 g, 2.29 mmol) in tetrahydrofuran ("THF") (1 mL) in one portion at 0° C. After 30 min, the cooling bath was removed, and the mixture was stirred at 23° C. for 7 h. $Bu_4NI$ (0.61 g, 1.65 mmol) in dimethylformamide ("DMF") (5 mL) was added, and, 15 min later, Bromomethyl Resin 6 (0.477 g) was added in one portion. The mixture was gently stirred for 64 h, and the solvent was removed by filtration. The resin was washed with THF (3×), DMF-$H_2O$ (2:1, 3×), DMF (3×), THF (3×), and DCM (3×), and was dried under vacuum to give light brown beads (0.455 g).

Example 4

Preparation of (Benzyloxymethyl)phenoxymethyl-polystyrene (9)

To a suspension of NaH (60% in mineral oil, 83 mg, 2.1 mmol) in THF (8 mL) was added benzyl alcohol (0.46 g, 4.3 mmol) at 23° C. After 1 d, this solution was added to a suspension of Bromomethyl Resin 6 (0.504 g) with Bu$_4$NI (38 mg, 0.10 mmol) in DMF (8 mL) at 23° C. The mixture was stirred gently for 1.5 d, and the solvent was removed by filtration. The resin was washed with THF (2×), DMF-H$_2$O (1:1, 3×), DMF (3×), THF (3×), H$_2$O (3×), DMF (3×), and THF (3×). The resin was dried under vacuum to give light brown beads (0.475 g).

Example 5

Immobilization of Rh$_2$(S-TBSP)$_4$ in Pyridine-resin 7

To a mixture of Pyridine—Resin 7 (48.6 mg) and Rh$_2$(S-TBSP)$_4$ (38.8 mg, 0.268 mmol) was added DCM (5.5 mL) at 23° C. The mixture was gently stirred for 9 min; then Pyridine—Resin 7 (9.4 mg) was added again; and the resulting mixture was further stirred gently for 3 h. Most of the solvent was removed by a pipet, and DCM (5 mL) was added. The mixture was gently stirred for 5 min, and then most of the DCM was removed by a pipet. This procedure was repeated two more times, and then the resin was transferred to a funnel and washed with DCM (6×). The resin was dried under vacuum to give purple beads (0.105 9).

Example 6

Immobilization of Rh$_2$(S-biTISP)$_2$ in Pyridine-resin 7

To a solution of Rh$_2$(S-biTISP)$_2$ (57 mg, 0.030 mmol) in toluene (4 mL) was added Pyridine-Resin 7 (76.3 mg) in one portion. The mixture was swirled on a shaker (400–500 rpm) at 23° C. for 7 h, and then the solvent was removed by filtration. The resin was washed with toluene (9×5 mL) and was dried under vacuum to give purple beads (0.118 g, loading of Rh$_2$(S-biTISP)$_2$=0.17 mmol/g)

Example 7

Immobilization of Rh$_2$(S-TBSP)$_4$ in Phenyl-resin 9

To a solution of Rh$_2$(S-TBSP)$_4$ (0.186 g, 0.128 mmol) in toluene (5 mL) was added Phenyl-Resin 9 (0.114 g). The mixture was swirled on a shaker (400–500 rpm) at 23° C. for 16 h. The solvent was removed by filtration. The resin was washed with toluene (10×5 mL) and was dried under vacuum to give light green beads (0.136 g).

Example 8

Immobilization of Rh$_2$(S-biTISP)$_2$ in Phenyl-resin 9

To a solution of Rh$_2$(S-biTISP)$_2$ (8.5 mg, 0.0045 mmol) in toluene (1 mL) was added Phenyl-Resin 9 (38.8 mg) in one portion, and then toluene (1 mL) was added. The mixture was swirled on a shaker (400–500 rpm) for 6 d. The solvent was removed by filtration. The resin was washed with toluene (5×) and was dried under vacuum to give green beads (44.7 mg).

Example 9

Immobilization of Rh$_2$(S-TBSP)$_4$ in Polystyrene-DMAP Resin

Rh$_2$(S-TBSP)$_4$ was immobilized in commercial polystyrene-DMAP resin ("PS-DMAP", Argonaut Technologies, Inc.) in accordance with the following Scheme 5.

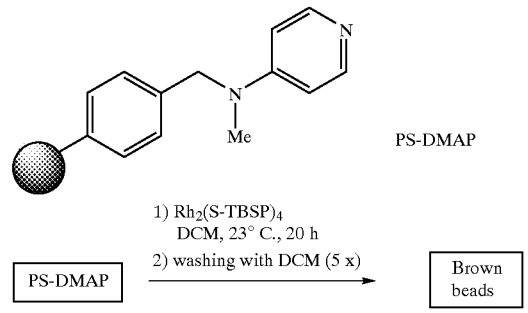

SCHEME 5

The polystyrene resin in PS-DMAP was cross-linked with 4% divinylbenzene, and the loading of the pyridyl group was 1.42 mmol/g. The product was obtained as brown beads and had a Rh$_2$(S-TBSP)$_4$ loading of 0.098 mmol/g.

Example 10

General Procedure for Cyclopropanation Reactions

A Buchner funnel with a fritted disc (fine porosity) was used as a reaction vessel. To facilitate efficient stirring of the reaction mixture with a magnetic stirring bar, the stem of the funnel was cut to about ½ inch. A positive pressure of argon gas was introduced through the stem of the funnel to prevent the reaction mixture from dripping through the disc. Rubber septa were used to seal the top and bottom of the funnel, and a needle was introduced through the top septum and connected via tubing to a bubbler to monitor evolution of gas from the reaction mixture.

Rh$_2$(S-biTISP)$_2$ immobilized Pyridine—Resin 7 (loading 0.17 mmol/g, 14.2 g, 0.0024 mmol) was put in the reaction vessel and argon gas was gently purged from the bottom for 10 min. Styrene (0.118 g, 1.13 mmol) in toluene (1 mL) was added. After 1 min, methyl phenyldiazoacetate (91.0 mg, 0.517 mmol) in toluene (1 mL) was added dropwise over 5 min at 23° C. with efficient stirring. After 13 min, the solvent was drained, and the resin was washed with toluene (5×5 mL). All of the filtrates were combined, and the cyclopropanation product was purified by preparative TLC (using hexanes/diethyl ether (2:1) as the eluent) to give white solid (0.470 mg, 91% yield). The enantiomeric excess was measured to be 85% by chiral HPLC with a (R,R)-Whelk-O column (using 2% isopropanol in hexanes as the eluent). The resin in the reaction vessel was dried under vacuum and was reused in the next cycle.

Although the invention has been described in detail for the purpose of illustration, it is understood that such detail is solely for that purpose, and variations can be made therein by those skilled in the art without departing from the spirit and scope of the invention which is defined by the claims that are set forth below.

What is claimed is:

1. A dirhodium catalyst composition comprising:
   a dirhodium catalyst which comprises a Rh—Rh moiety and four bridging ligand moieties; and
   a solid support, wherein said dirhodium catalyst and said solid support are bound together and wherein said dirhodium catalyst and said solid support are not covalently bound together via one or more of said bridging ligand moieties.

2. A composition according to claim 1, wherein each of the four ligand moieties are independently selected from carboxylate moieties and amide moieties.

3. A composition according to claim 1, wherein said dirhodium catalyst is a dirhodium tetracarboxylate catalyst.

4. A composition according to claim 1, wherein said dirhodium catalyst is a dirhodium tetracarboxamidate catalyst.

5. A composition according to claim 1, wherein said solid support is a macroporous solid support.

6. A composition according to claim 1, wherein said solid support is a cross-linked polystyrene resin.

7. A composition according to claim 1, wherein said solid support is a macroporous cross-linked polystyrene resin.

8. A composition according to claim 1, wherein said solid support is a cross-linked polystyrene resin and wherein the cross-linked polystyrene resin is more highly cross-linked than a 1% cross-linked polystyrene resin.

9. A composition according to claim 1, wherein said solid support is a cross-linked polystyrene resin comprising pendant groups having the formula:

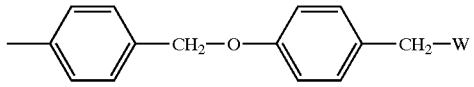

wherein W represents H, halogen, a hydroxy group, a thiol group, an alkoxy group, an alkylthio group, an aryl thio group, or combinations thereof.

10. A composition according to claim 9, wherein W represents a hydroxyl group, a halogen, or an alkoxy group.

11. A composition according to claim 9, wherein W represents an alkoxy group.

12. A composition according to claim 9, wherein W represents a —OW' group and wherein W' is an aryl group.

13. A composition according to claim 9, wherein W represents a —OW' group and wherein W' is a substituted or unsubstituted phenyl group or a substituted or unsubstituted pyridyl group.

14. A composition according to claim 9, wherein W represents a —OW' group and wherein W' is a phenyl group or 4-pyridyl group.

15. A composition according to claim 9, wherein W represents a —OW' group and wherein W' is nitrogen-containing heterocycle.

16. A composition according to claim 15, wherein the nitrogen-containing heterocycle is a pyridyl group, a quinolinyl group, an isoquinolinyl group, an imidazolyl group, or a benzimidazolyl group.

17. A composition according to claim 1, wherein said solid support is a cross-linked polystyrene resin comprising pendant groups having the formula:

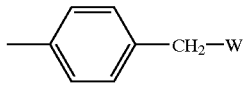

wherein W represents H, halogen, a hydroxy group, a thiol group, an alkoxy group, an alkylthio group, an aryl thio group, or combinations thereof.

18. A composition according to claim 1, wherein said solid support comprises a nitrogen-containing heterocyclic pendant group.

19. A composition according to claim 18, wherein the nitrogen-containing heterocyclic pendant group is a pyridyl group, a quinolinyl group, an isoquinolinyl group, an imidazolyl group, or a benzimidazolyl group.

20. A composition according to claim 1, wherein said solid support comprises a nitrogen-containing heterocyclic pendant group and wherein said dirhodium catalyst and said solid support are bound together via a bond between at least one of the rhodiums' axial positions and the heterocyclic pendant group's nitrogen.

21. A composition according to claim 1, wherein said solid support comprises a pendant substituted or unsubstituted phenyl group.

22. A composition according to claim 1, wherein said dirhodium catalyst is a chiral dirhodium catalyst.

23. A composition according to claim 1, wherein said dirhodium catalyst is a chiral dirhodium tetracarboxylate catalyst.

24. A composition according to claim 1, wherein said dirhodium catalyst is a chiral dirhodium tetracarboxamidate catalyst.

25. A composition according to claim 1, wherein said dirhodium catalyst has the formula:

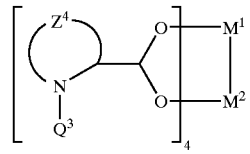

wherein each of $M^1$ and $M^2$ is Rh; $Z^4$ represents the atoms necessary to complete a 3–12 membered heterocyclic ring; and $Q^3$ is an electron withdrawing group.

26. A composition according to claim 25, wherein $Z^4$ has the formula —$CH_2CH_2CH_2$—.

27. A composition according to claim 25, wherein said dirhodium tetracarboxylate catalyst has one of the following formulae:

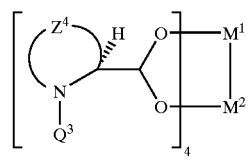 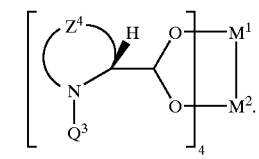

28. A composition according to claim 25, wherein said dirhodium tetracarboxylate catalyst has $D_2$ symmetry.

29. A composition according to claim 1, wherein said dirhodium catalyst is a dirhodium tetracarboxylate catalyst having the formula:

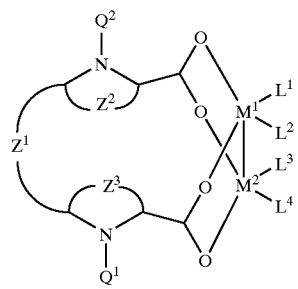

wherein each of $M^1$ and $M^2$ is Rh; $Z^2$ and $Z^3$, independently, are the atoms necessary to complete a 3–12 membered heterocyclic ring; $Z^1$ is an alkylene or arylene group; $Q^1$ and $Q^2$ are the same or different and are electron withdrawing groups; $L^1$ and $L^3$, taken together, represent —O—$CR^{13}$—O—; $L^2$ and $L^4$, taken together, represent —O—$CR^{14}$—

O—; and $R^{13}$ and $R^{14}$ are the same or different and are selected from the group consisting of alkyl groups and aryl groups or $R^{13}$ and $R^{14}$ represent alkylene or arylene groups that are directly or indirectly bonded to one another.

30. A composition according to claim 29, wherein said dirhodium tetracarboxylate catalyst has the formula:

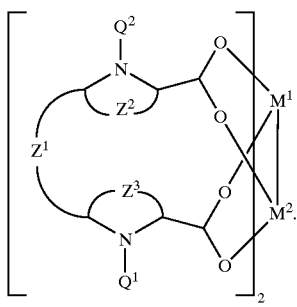

31. A composition according to claim 29, wherein $Z^2$ and $Z^3$ each have the formula —$CH_2CH_2$—.

32. A composition according to claim 29, wherein $Z^1$ is a 1,3-phenylene moiety.

33. A composition according to claim 29, wherein said dirhodium tetracarboxylate catalyst has one of the following formulae:

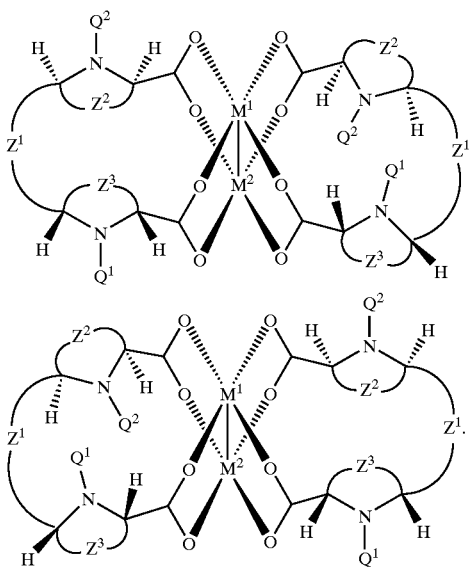

34. A composition according to claim 29, wherein said dirhodium tetracarboxylate catalyst has one of the following formulae:

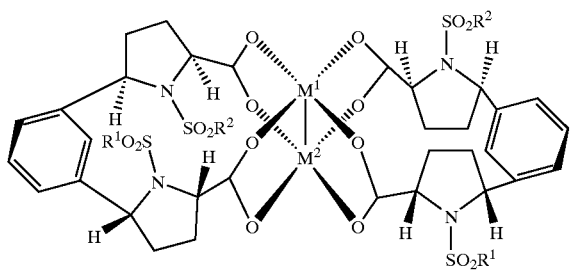

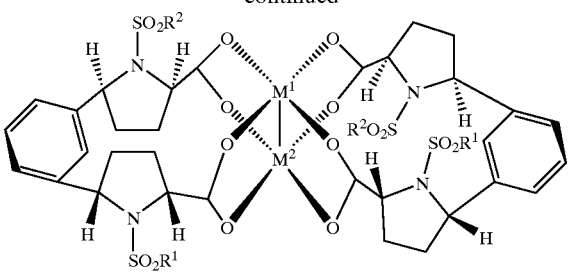

wherein $R^1$ and $R^2$ are the same or different and are alkyl or aryl groups.

35. A composition according to claim 1, wherein said dirhodium catalyst has the following formula:

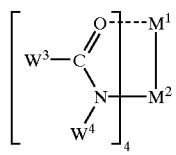

wherein each of $M^1$ and $M^2$ is Rh; $W^3$ represents an alkyl group, an aryl group, an alkoxy group, or an amine group; $W^4$ represents an alkyl group or an aryl group; or $W^3$ and $W^4$, taken together, represent the atoms necessary to complete a 3–12 membered heterocyclic ring.

36. A method for making a dirhodium catalyst composition according to claim 1, said method comprising:
  providing a dirhodium catalyst which comprises a Rh—Rh moiety and four bridging ligand moieties; and
  contacting the dirhodium catalyst with a solid support under conditions effective to bind the dirhodium catalyst and the solid support together and to produce the dirhodium catalyst composition.

37. A method according to claim 36, wherein each of the four bridging ligand moieties are independently selected from carboxylate moieties and amide moieties.

38. A method according to claim 36, wherein the dirhodium catalyst is a dirhodium tetracarboxylate catalyst.

39. A method according to claim 36, wherein the dirhodium catalyst is a dirhodium tetracarboxamidate catalyst.

40. A method according to claim 36, wherein the dirhodium catalyst is a chiral dirhodium catalyst.

41. A method according to claim 36, wherein the dirhodium catalyst has the formula:

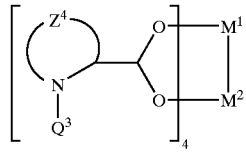

wherein each of $M^1$ and $M^2$ is Rh; $Z^4$ represents the atoms necessary to complete a 3–12 membered heterocyclic ring; and $Q^3$ is an electron withdrawing group.

42. A method according to claim 41, wherein $Z^4$ has the formula —$CH_2CH_2CH_2$—.

43. A method according to claim 41, wherein the dirhodium tetracarboxylate catalyst has one of the following formulae:

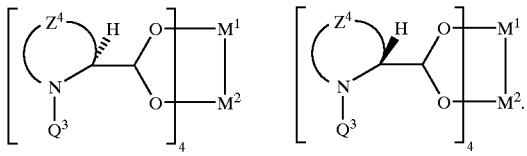

44. A method according to claim 41, wherein the dirhodium tetracarboxylate catalyst has $D_2$ symmetry.

45. A method according to claim 36, wherein the dirhodium tetracarboxylate catalyst has the formula:

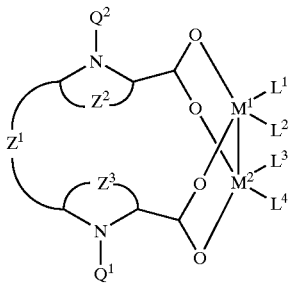

wherein each of $M^1$ and $M^2$ is Rh; $Z^2$ and $Z^3$, independently, are the atoms necessary to complete a 3–12 membered heterocyclic ring; $Z^1$ is an alkylene or arylene group; $Q^1$ and $Q^2$ are the same or different and are electron withdrawing groups; $L^1$ and $L^3$, taken together, represent —O—CR$^{13}$—O—; $L^2$ and $L^4$, taken together, represent —O—CR$^{14}$—O—; and $R^{13}$ and $R^{14}$ are the same or different and are selected from the group consisting of alkyl groups and aryl groups or $R^{13}$ and $R^{14}$ represent alkylene or arylene groups that are directly or indirectly bonded to one another.

46. A method according to claim 45, wherein the dirhodium tetracarboxylate catalyst has the formula:

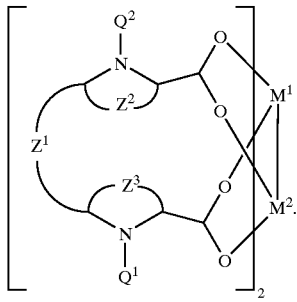

47. A method according to claim 45, wherein $Z^2$ and $Z^3$ each have the formula —CH$_2$CH$_2$—.

48. A method according to claim 45, wherein $Z^1$ is a 1,3-phenylene moiety.

49. A method according to claim 45, wherein the dirhodium tetracarboxylate catalyst has one of the following formulae:

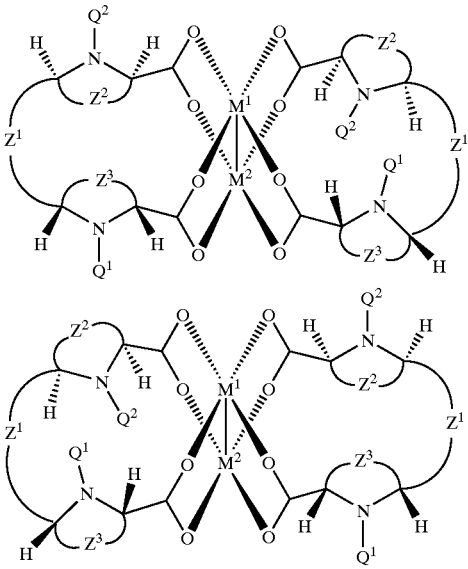

50. A method according to claim 45, wherein the dirhodium tetracarboxylate catalyst has one of the following formulae:

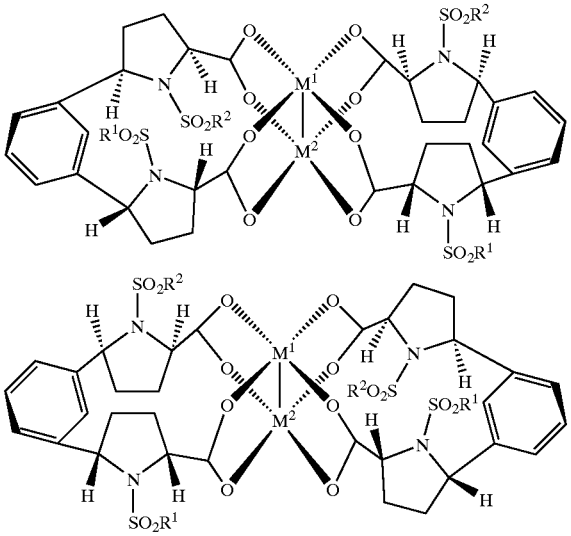

wherein $R^1$ and $R^2$ are the same or different and are alkyl or aryl groups.

51. A method according to claim 36, wherein the solid support comprises a nitrogen-containing heterocyclic pendant group.

52. A method according to claim 51, wherein the nitrogen containing heterocyclic pendant group is a pyridyl group, a quinolinyl group, an isoquinolinyl group, an imidazolyl group, or a benzimidazolyl group.

53. A method according to claim 36, wherein the solid support comprises a nitrogen-containing heterocyclic pendant group and wherein the dirhodium catalyst and the solid support are bound together via a bond between at least one of the rhodiums' axial positions and the heterocyclic pendant group's nitrogen.

54. A method according to claim 36, wherein the solid support comprises a pendant substituted or unsubstituted phenyl group.

* * * * *